United States Patent [19]

Fink et al.

[11] Patent Number: 5,312,735

[45] Date of Patent: May 17, 1994

[54] SUPERSECRETING MUTANTS OF SACCHAROMYCES CEREVISIAE

[75] Inventors: Gerald R. Fink, Chestnut Hill, Mass.; Catherine M. Buckley, Cork, Ireland

[73] Assignee: Collaborative Research, Inc., Bedford, Mass.

[21] Appl. No.: 960,245

[22] Filed: Oct. 13, 1992

Related U.S. Application Data

[63] Continuation of Ser. No. 379,613, Jul. 13, 1989, abandoned, which is a continuation-in-part of Ser. No. 294,198, Jan. 6, 1989, abandoned.

[51] Int. Cl.$^5$ .................. C12N 15/00; C12N 1/16; C12N 1/18
[52] U.S. Cl. ................. 435/69.1; 435/122.3; 435/254.21
[58] Field of Search ............ 435/172.3, 255, 256, 435/69.1, 215; 536/27, 23.5; 935/49, 50

[56] References Cited

U.S. PATENT DOCUMENTS

| | | | |
|---|---|---|---|
| 4,546,082 | 10/1985 | Kurjan et al. | 435/172.3 |
| 4,929,553 | 5/1990 | Bussey et al. | 435/172.3 |
| 4,931,373 | 6/1990 | Kawasaki et al. | 435/69.2 |
| 4,937,189 | 6/1990 | Davidow et al. | 435/69.1 |
| 5,032,681 | 7/1991 | Friden et al. | 536/27 |
| 5,057,416 | 10/1991 | Smith et al. | 435/69.1 |

FOREIGN PATENT DOCUMENTS 201208 11/1986 European Pat. Off. .

OTHER PUBLICATIONS

Bussey et al., *Curr. Genet.*, 7(6):449–56, 1983.
Serrano, R. et al., *Nature*, 319:689–93, 1986.
Orr-Weaver, T. L. et al., *Methods In Enzymology*, 101:228–245, 1983.
Rothstein, R. J., *Methods in Enzymology*, 101:202–211, 1983.
Smith, R. A., *Science*, 229:1219–1224, 1985.
Rose, M. D., *Methods in Enzymology*, 152:481–504, 1987.
Biotechnology Abstracts 84–00948: Bussey et al., *Curr. Genet.*, 7(6):449–56, 1983.
Tsai, P.-K. et al., *J. Biol. Chem.*, 259(6):3805–11, 1984.

*Primary Examiner*—Robert J. Hill, Jr.
*Assistant Examiner*—Marianne Porta Allen
*Attorney, Agent, or Firm*—Wolf, Greenfield & Sacks

[57] ABSTRACT

This invention relates to the production of useful protein products by secretion from yeast cells. In particular, it relates to the identification of supersecreting mutant yeast cells, isolation of the wild-type gene which complements the mutation, and construction of non-leaky, non-reverting supersecreting strains.

3 Claims, 14 Drawing Sheets ss-secretion signal
P-promoter
T-terminator

H-HindIII
E-EcoRI
C-ClaI
S-SalI

Legend to the figure:

|—————| = 1 kb of DNA

E = EcoRI
B = BamHI
H = HindIII

▬▬▬ = YCp50 vector
——— = SSC1 gene region insert into YCp50

```
         10         20         30         40         50         60
          *          *          *          *          *          *
TAG TAA CTA TAA TAT CCT TAC GAC TGG GCA AGA CAA GAC GAA GCA AGG CCA GCA CAG 70         80         90        100        110        120
          *          *          *          *          *          *
ACG TAA GCT TAA GTG TAA AAA GAT GTA AAG ATA ATT ATG AGT GAC AAT CCA TTT AAT GCG
                                         Met Ser Asp Asn Pro Phe Asn Ala 130        140        150        160        170        180
          *          *          *          *          *          *
AGT CTT GAC GAG GAC AAC CGT TCA AAC CGT GAG AGA GAA ATA CTA GAT GCC ACA GAG GCC
Ser Leu Asp Glu Asp Asn Arg Ser Asn Arg Glu Arg Glu Ile Leu Asp Ala Thr Glu Ala 190        200        210        220        230        240
          *          *          *          *          *          *
CTT TCG AAA CCA AGC CCT TCT TTA GAG TAT TGT ACT TTA TCC GTG GAC GAA GCT CTA GAA
Leu Ser Lys Pro Ser Pro Ser Leu Glu Tyr Cys Thr Leu Ser Val Asp Glu Ala Leu Glu 250        260        270        280        290        300
          *          *          *          *          *          *
AAA CTG GAC ACT GAC AAA AAC GGT GGT GGA TCA TCG AAC GAG GCC AAC AAT AGG AGA
Lys Leu Asp Thr Asp Lys Asn Gly Gly Gly Ser Ser Asn Glu Ala Asn Asn Arg Arg 310        320        330        340        350        360
          *          *          *          *          *          *
TCA CTT TAT GGC CCC AAT GAA ATA ACC GTA GAA GAT GAT GAA AGT CTT TTC AAG AAG TTC
Ser Leu Tyr Gly Pro Asn Glu Ile Thr Val Glu Asp Asp Glu Ser Leu Phe Lys Lys Phe 370        380        390        400        410        420
          *          *          *          *          *          *
TTG TCA AAT TTC ATT GAG GAT CGA ATG CTA ATT CTA TTA GGA TCC GCA GTG GTC TCT
Leu Ser Asn Phe Ile Glu Asp Arg Met Ile Leu Leu Ile Gly Ser Ala Val Val Ser 430        440        450        460        470        480
          *          *          *          *          *          *
CTT TTT ATG GGT AAC ATT GAT GAT GCT GTT AGT ATC ACA GCC ATT TTC ATA GTT GTC
Leu Phe Met Gly Asn Ile Asp Asp Ala Val Ser Ile Thr Ala Ile Phe Ile Val Val
```

Fig. 5A

```
                490         500         510         520         530         540
                 *           *           *           *           *           *
ACT GTC GGT TTT GTC CAA GAA TAT AGG TCT GAA AAA TCT CTA GAA GCG TTG AAT AAA TTG
Thr Val Gly Phe Val Gln Glu Tyr Arg Ser Glu Lys Ser Leu Glu Ala Leu Asn Lys Leu 550         560         570         580         590         600
                 *           *           *           *           *           *
GTT CCT GCT GAA TGT CAC TTA ATG AGA TGT GGT CAA AGT CAT GAG AGT CTG GCT TCC ACC
Val Pro Ala Glu Cys His Leu Met Arg Cys Gly Gln Ser His Glu Val Leu Ala Ser Thr 610         620         630         640         650         660
                 *           *           *           *           *           *
TTG GTT CCT GGT GAT TTA GTG CAC TTC AGA ATA GGT GAC AGA ATC CCC GCA GAC ATT AGA
Leu Val Pro Gly Asp Leu Val His Phe Arg Ile Gly Asp Arg Ile Pro Ala Asp Ile Arg 670         680         690         700         710         720
                 *           *           *           *           *           *
ATT ATT GAA GCA ATC GAT TTA TCC ATC GAT GAA AGT AAT TTA ACT GGT GAA AAT GAA CCG
Ile Ile Glu Ala Ile Asp Leu Ser Ile Asp Glu Ser Asn Leu Thr Gly Glu Asn Glu Pro 730         740         750         760         770         780
                 *           *           *           *           *           *
GTA CAT AAA ACC TCA CAA ACG ATC GAA AAA TCT TCC TTT AAC GAT CAG CCT AAT TCA ATT
Val His Lys Thr Ser Gln Thr Ile Glu Lys Ser Ser Phe Asn Asp Gln Pro Asn Ser Ile 790         800         810         820         830         840
                 *           *           *           *           *           *
GTA CCG ATT TCT GAG AGA TCT TGT ATA GCT TAT ATG GGT ACA TTA GTC AAG GAA GGT CAT
Val Pro Ile Ser Glu Arg Ser Cys Ile Ala Tyr Met Gly Thr Leu Val Lys Glu Gly His 850         860         870         880         890         900
                 *           *           *           *           *           *
GGT AAG GGT ATC GTC GTA GGA ACA GGT ACA AAC ACA TCC TTT GGT GCC GTT TTT GAA ATG
Gly Lys Gly Ile Val Val Gly Thr Gly Thr Asn Thr Ser Phe Gly Ala Val Phe Glu Met
```

```
           910            920            930            940            950            960
            *              *              *              *              *              *
ATG AAT AAT ATT GAA AAA CCG AAG ACT CCA TTG CAG TTA ACA ATG GAC AAA TTG GGA AAG
Met Asn Asn Ile Glu Lys Pro Lys Thr Pro Leu Gln Leu Thr Met Asp Lys Leu Gly Lys 970            980            990           1000           1010           1020
            *              *              *              *              *              *
GAC TTG TCA CTG GTT AGC TTC ATA GTT ATT GGT ATG ATT TGT TTA GTT GGT ATC ATA CAA
Asp Leu Ser Leu Val Ser Phe Ile Val Ile Gly Met Ile Cys Leu Val Gly Ile Ile Gln 1030           1040           1050           1060           1070           1080
            *              *              *              *              *              *
GGT AGA TCT TGG TTA GAA ATG TTC CAA ATA TCG GTA TCC TTA GCG GTT GCT GCT ATT CCA
Gly Arg Ser Trp Leu Glu Met Phe Gln Ile Ser Val Ser Leu Ala Val Ala Ala Ile Pro 1090           1100           1110           1120           1130           1140
            *              *              *              *              *              *
GAA GGG TTA CCA ATT ATT GTC ACT GTT ACT TTG GCA TTG GGT GTT CTG AGA ATG GCC AAG
Glu Gly Leu Pro Ile Ile Val Thr Val Thr Leu Ala Leu Gly Val Leu Arg Met Ala Lys 1150           1160           1170           1180           1190           1200
            *              *              *              *              *              *
CGT AAA GCC ATC GTG AGA AGG TTA CCA AGT GTC GAA ACT TTA GGC TCT GTC AAC GTT ATC
Arg Lys Ala Ile Val Arg Arg Leu Pro Ser Val Glu Thr Leu Gly Ser Val Asn Val Ile 1210           1220           1230           1240           1250           1260
            *              *              *              *              *              *
TGC TCC GAC AAA ACA GGT ACA CTA ACC TCA AAC CAC ATG ACC GTA TCT AAA CTT TGG TGC
Cys Ser Asp Lys Thr Gly Thr Leu Thr Ser Asn His Met Thr Val Ser Lys Leu Trp Cys 1270           1280           1290           1300           1310           1320
            *              *              *              *              *              *
TTG GAC AGT ATG TCC AAT AAG CTA AAC GTC CTC TCA TTA GAC AAA AAT AAG AAG ACT AAA
Leu Asp Ser Met Ser Asn Lys Leu Asn Val Leu Ser Leu Asp Lys Asn Lys Lys Thr Lys
```

```
      1330            1340            1350            1360            1370            1380
        *               *               *               *               *               *
AAT TCT AAT GGA AAT TTG AAA AAC TAT TTG ACT GAA GAC GTT AGG GAA ACT CTA ACT ATC
Asn Ser Asn Gly Asn Leu Lys Asn Tyr Leu Thr Glu Asp Val Arg Glu Thr Leu Thr Ile 1390            1400            1410            1420            1430            1440
        *               *               *               *               *               *
GGT AAT CTC TGT AAT AAT GCA TCT TTC TCT CAA GAA CAT GCC ATA TTT CTG GGA AAT CCT
Gly Asn Leu Cys Asn Asn Ala Ser Phe Ser Gln Glu His Ala Ile Phe Leu Gly Asn Pro 1450            1460            1470            1480            1490            1500
        *               *               *               *               *               *
ACT GAT GTA GCT CTT TTA GAG CAA TTG GCA AAC TTT GAA ATG CCT GAT ATC AGA AAC ACC
Thr Asp Val Ala Leu Leu Glu Gln Leu Ala Asn Phe Glu Met Pro Asp Ile Arg Asn Thr 1510            1520            1530            1540            1550            1560
        *               *               *               *               *               *
GTT CAA AAA GTT CAG GAA CTT CCA TTT AAC TCG AAA AGA AAA TTA ATG GCA ACC AAG ATT
Val Gln Lys Val Gln Glu Leu Pro Phe Asn Ser Lys Arg Lys Leu Met Ala Thr Lys Ile 1570            1580            1590            1600            1610            1620
        *               *               *               *               *               *
CTC AAC CCT GTC GAC AAT AAG TGT ACA GTT TAT GTT AAA GGT GCA TTT GAA AGA ATT CTT
Leu Asn Pro Val Asp Asn Lys Cys Thr Val Tyr Val Lys Gly Ala Phe Glu Arg Ile Leu 1630            1640            1650            1660            1670            1680
        *               *               *               *               *               *
GAG TAC TCC ACA AGT TAT TTG AAA TCA AAG GGT AAA AAA ACT GAA AAG TTG ACT GAA GCC
Glu Tyr Ser Thr Ser Tyr Leu Lys Ser Lys Gly Lys Lys Thr Glu Lys Leu Thr Glu Ala 1690            1700            1710            1720            1730            1740
        *               *               *               *               *               *
CAA AAA GCT ACG ATA AAT GAG TGC GCA AAT TCT ATG GCA TCT GAA GGT TTG CGT GTC TTT
Gln Lys Ala Thr Ile Asn Glu Cys Ala Asn Ser Met Ala Ser Glu Gly Leu Arg Val Phe
```

FIG. 5D

```
      1750        1760        1770        1780        1790        1800
        *           *           *           *           *           *
GGA TTT GCT AAA CTA ACT TTG TCT GAT TCA TCA ACT CCT CTA ACC GAA GAC CTA ATC AAA
Gly Phe Ala Lys Leu Thr Leu Ser Asp Ser Ser Thr Pro Leu Thr Glu Asp Leu Ile Lys 1810        1820        1830        1840        1850        1860
        *           *           *           *           *           *
GAT TTA ACC TTT ACT GGT TTA ATC GGT ATG AAT GAC CCA CCA AGA CCG AAC GTT AAA TTT
Asp Leu Thr Phe Thr Gly Leu Ile Gly Met Asn Asp Pro Pro Arg Pro Asn Val Lys Phe 1870        1880        1890        1900        1910        1920
        *           *           *           *           *           *
GCC ATC GAA CAA TTA CTA CAA GGT GTC CAT ATT ATT ATG ATC ACT GGT GAT TCT GAG
Ala Ile Glu Gln Leu Leu Gln Gly Val His Ile Ile Met Ile Thr Gly Asp Ser Glu 1930        1940        1950        1960        1970        1980
        *           *           *           *           *           *
AAT ACC GCA GTA AAC ATT GCA AAA CAA ATT GGT ATT CCA GTT ATT GAT CCA AAG CTT TCC
Asn Thr Ala Val Asn Ile Ala Lys Gln Ile Gly Ile Pro Val Ile Asp Pro Lys Leu Ser 1990        2000        2010        2020        2030        2040
        *           *           *           *           *           *
GTT TTA TCC GGT GAT AAA TTA GAT GAA ATG TCA GAT GAT CAA CTG GCC AAT GTC ATC GAC
Val Leu Ser Gly Asp Lys Leu Asp Glu Met Ser Asp Asp Gln Leu Ala Asn Val Ile Asp 2050        2060        2070        2080        2090        2100
        *           *           *           *           *           *
CAC GTT AAT ATT TTT GCT CGT GCT ACG CCT GAG CAT CCT GAG CAT AAG TTA AAC ATT GTT CGT GCA TTA
His Val Asn Ile Phe Ala Arg Ala Thr Pro Glu His Lys Leu Asn Ile Val Arg Ala Leu 2110        2120        2130        2140        2150        2160
        *           *           *           *           *           *
AGA AAG AGG GAT GTG GTA GCA ATG ACT GGT GAT GGT GTT AAC GAC CCT GCG TTG
Arg Lys Arg Asp Val Val Ala Met Thr Gly Asp Gly Val Asn Asp Pro Ala Leu Leu
```

FIG. 5E

```
     2170            2180            2190            2200            2210            2220
       *               *               *               *               *               *
AAA CTT TCA GAT ATT GGT GTT TCT ATG GGT AGA ATT GGT ACA GAT GTA GCC AAA GAA GCC
Lys Leu Ser Asp Ile Gly Val Ser Met Gly Arg Ile Gly Thr Asp Val Ala Lys Glu Ala 2230            2240            2250            2260            2270            2280
       *               *               *               *               *               *
TCA GAT ATG GTC TTA ACT GAT GAT GAC TTC AGT ACT ATT TTA ACT GCC ATT GAA GAG GGT
Ser Asp Met Val Leu Thr Asp Asp Asp Phe Ser Thr Ile Leu Thr Ala Ile Glu Glu Gly 2290            2300            2310            2320            2330            2340
       *               *               *               *               *               *
AAA GGT ATC TTT AAT AAT ATT CAG AAT TTC CTG ACT TTT CAA TTG TCT ACT TCT GTT GCC
Lys Gly Ile Phe Asn Asn Ile Gln Asn Phe Leu Thr Phe Gln Leu Ser Thr Ser Val Ala 2350            2360            2370            2380            2390            2400
       *               *               *               *               *               *
GCA CTA TCA GTT GCA CTA TCT ACA GCG TTT AAA CTA CCC AAT CCA CTG AAC GCA ATG
Ala Leu Ser Leu Val Ala Leu Ser Thr Ala Phe Lys Leu Pro Asn Pro Leu Asn Ala Met 2410            2420            2430            2440            2450            2460
       *               *               *               *               *               *
CAA ATT CTT TGG ATA AAT ATT TTA ATG GAT GGG CCA CCA GCT CAA TCC TTA GGT GTG GAA
Gln Ile Leu Trp Ile Asn Ile Leu Met Asp Gly Pro Pro Ala Gln Ser Leu Gly Val Glu 2470            2480            2490            2500            2510            2520
       *               *               *               *               *               *
CCT GTT GAT CAT GAA GTT ATG AAA CCT CCA AGA AAA CGT ACC GAT AAA ATT TTG ACC
Pro Val Asp His Glu Val Met Lys Pro Pro Arg Lys Arg Thr Asp Lys Ile Leu Thr 2530            2540            2550            2560            2570            2580
       *               *               *               *               *               *
CAT GAT GTA ATG AAA CGT TTA CTA ACC ACC GCG GCC TGT ATC ATC GTT GGG ACA GTT TAC
His Asp Val Met Lys Arg Leu Leu Thr Thr Ala Ala Cys Ile Ile Val Gly Thr Val Tyr

FIG. 5F
```

```
        2590        2600        2610        2620        2630        2640
          *           *           *           *           *           *
ATT TTT GTT AAA GAG ATG GCC GAA GAT GGT AAA GTA ACT GCT AGA GAT ACT ATG ACA
Ile Phe Val Lys Glu Met Ala Glu Asp Gly Lys Val Thr Ala Arg Asp Thr Met Thr 2650        2660        2670        2680        2690        2700
          *           *           *           *           *           *
TTT ACT TGT TTT GTT TTT TTT GAT ATG TTT AAT GCT TTG GCC TGC AGA CAT AAC AAG
Phe Thr Cys Phe Val Phe Phe Asp Met Phe Asn Ala Leu Ala Cys Arg His Asn Lys 2710        2720        2730        2740        2750        2760
          *           *           *           *           *           *
TCA ATC TTC GAA ATC GGC TTT TTC ACG AAC AAA ATG TTC AAC TAC GCC GTT GGA TCT
Ser Ile Phe Glu Ile Gly Phe Phe Thr Asn Lys Met Phe Asn Tyr Ala Val Gly Ser 2770        2780        2790        2800        2810        2820
          *           *           *           *           *           *
CTG TTA GGT CAA ATG TGC GCT ATA TAT ATA CCA TTT TTC CAA AGT ATC TTT AAA ACT GAG
Leu Leu Gly Gln Met Cys Ala Ile Tyr Ile Pro Phe Phe Gln Ser Ile Phe Lys Thr Glu 2830        2840        2850        2860        2870        2880
          *           *           *           *           *           *
AAA CTT GGT ATC TCT GAT ATA CTA TTG TTA TTG CTC ATC AGC AGT AGC GTT TTC ATC GTT
Lys Leu Gly Ile Ser Asp Ile Leu Leu Leu Leu Leu Ile Ser Ser Ser Val Phe Ile Val 2890        2900        2910        2920        2930        2940
          *           *           *           *           *           *
GAT GAA TTG AGA AAA TTG TGG ACG AGG AAA AAG AAT GAA GAA GAC TCA ACG TAT TTC TCA
Asp Glu Leu Arg Lys Leu Trp Thr Arg Lys Lys Asn Glu Glu Asp Ser Thr Tyr Phe Ser 2950        2960        2970        2980        2990        3000
          *           *           *           *           *           *
AAT GTT TGA TAT GTC ACA TTT TGT GCT TTT ATC GTT TTT CCT TCC TTC CCT TTA TCT TTC
Asn Val ---
```

FIG. 5G

```
            3010            3020            3030            3040            3050            3060
             *               *               *               *               *               *
ATG AGG ACG CCC AAC CCT ATT GAG GTA AAT GTA CTA ATT AAT GGG AAC ATA TGT AGA TGT 3070            3080            3090            3100            3110            3120
             *               *               *               *               *               *
ATA TAT GTA CAT ATA TTT ACA ACG GAT ACT AAG ATA AAC ATG TAT GGG CGA CTT TTC GTA 3130            3140            3150            3160            3170            3180
             *               *               *               *               *               *
TAT ACA AAG CAA TAT AAA ATT TTA TTC TTT CCT TCT TTT CCC GGA CTA GAT ATA AAA TCT 3190            3200            3210            3220            3230            3240
             *               *               *               *               *               *
CCG TAA TCA GTG GTT ATG ATT TTC AAA AGT TAA TCA CAG TTT TAT TTA AAA CTG TAT ACA 3250            3260            3270            3280            3290            3300
             *               *               *               *               *               *
ATT ATT TGC AGC CGC CTT TCG CAA TCT GTT CAT AAC AGC TAA TCC TTC TCC TTC CTC ATT 3310            3320            3330            3340            3350            3360
             *               *               *               *               *               *
TAT ACC TTC GAC AAA TAT TAG GTC TAC TTT ATC ATT TTC ATC CAC TTT TCT TAA AGC TGC
```

FIG. 5H

SUPERSECRETING MUTANTS OF SACCHAROMYCES CEREVISIAE

RELATED APPLICATION

This application is a continuation of U.S. patent application Ser. No. 07/379,613 filed Jul. 13, 1989, now abandoned, continuation-in-part of U.S. patent application Ser. No. 07/294,198 filed Jan. 6, 1989 now abandoned.

BACKGROUND OF THE INVENTION

Yeast cells have proven useful as hosts for production of heterologous gene products. Yeasts such as the bakers yeast *Saccharomyces cerevisiae* can be grown to high cell densities inexpensively in simple media, and helpful genetic techniques and molecular genetic methods are available. Accordingly, pharmaceutical preparations of human alpha-1-antitrypsin, and vaccines for hepatitis B virus have been produced in the cytoplasm of yeast cells and isolated by lysis of cells and purification of the desired protein (Valenzuela, P., et al., 1982, Nature 298: 347-350; Travis, J., et al., 1985, J. Biol. Chem. 260: 4384-4389). However, some proteins, such as prochymosin and prourokinase (also known as single-chain urinary plasminogen activator, or scu-PA) are produced much more efficiently by secretion from yeast cells, apparently because they are normally secreted from their native host cells and because proper folding of the polypeptide chain and disulfide bond formation occur only in the secretion pathway (Smith, Duncan, & Moir, 1985, Science 229: 1219-1224; Moir et al., 1988, Abstract 19 from The Ninth International Congress on Fibrinolysis, Amsterdam, The Netherlands).

Yields of secreted heteroloqous proteins from yeast fermentations have been limited. Most non-yeast proteins are secreted quite inefficiently from yeast cells. For example, in all of the following cases, at least as much of the heteroloqous protein is found inside the cell as is found outside the cell in the culture broth or between the cell membrane and wall. This is true for calf prochymosin (Smith, Duncan, & Moir, 1985, Science 229: 1219-1223), human alpha-1-antitrypsin (Moir & Dumais, 1987, Gene 56: 209-217), human tissue plasminogen activator (Lemontt et al., 1985, DNA 4: 419-428), anchor-minus influenza hemagglutinin (Jabbar & Nayak, 1987, Mol. Cell. Biol. 7: 1476-1485), alpha interferon (Hitzeman et al., 1983, Science 219: 620-625), a consensus interferon (Zsebo et al., 1986, J. Biol. Chem. 261: 5858-5865), murine lambda and mu immunoglobulin chains (Wood et al., 1985, Nature 314: 446-449), and human lysozyme (Jigami et al., 1986, Gene 43: 273-279). Clearly, methods are needed to increase the efficiency of secretion of these proteins and other non-yeast proteins from yeast cells. Such methods would provide therapeutic and industrially useful proteins more economically.

Duncan and Smith (1986, European Patent Application EP 201208 Apr. 8, 1986) have taught methods for increasing the yields of heteroloqous proteins secreted from yeast by mutating yeast cells and screening for the desired mutant cells. These methods are effective and result in new yeast strains bearing many different "supersecreting" mutations, including for example ssc1, ssc2, and ssc3, which significantly increase the yield of secreted heteroloqous proteins. However, these mutations were obtained by chemical mutagenesis methods applied to living yeast cells, and such methods do not insure that the resulting mutations will be non-leaky or non-reverting. Furthermore, these methods do not distinguish between mutations which yield a non-functional gene product and those which yield a gene product with an altered function.

Leaky mutations are those which "fail to shut off completely the activity of a gene so that some residual expression of its function remains" (W. Hayes, 1968, "The Genetics of Bacteria and their Viruses, 2nd ed., John Wiley & Sons, Inc., N.Y., p.320). Non-leaky mutations in SSC genes which do shut off completely the activity of a gene to make it non-functional, would be expected to yield better supersecreting strains because the activity of the SSC gene will be totally eliminated.

Many mutations induced by chemical means applied to whole living cells, as taught by Duncan and Smith (1986, supra), are point mutations involving a single nucleoside change. In contrast to deletions and disruptions of DNA sequences, such point mutations are frequently leaky mutations. Furthermore, many point mutations may be reverted by true reversion to the wild-type gene or the phenotype may be reversed by various types of suppression. Supersecreting mutations which could not undergo true reversion or be suppressed by frame-shift, nonsense, or intragenic suppressors would be useful, and methods providing such mutations would be helpful for improving secretion of heteroloqous proteins by yeast cells.

In summary the mutations of Duncan and Smith (1986, supra) are useful, but the methods taught for obtaining these mutants do not reliably provide non-leaky, non-reverting supersecreting strains, and as a result may not provide the most useful forms of supersecreting strains.

SUMMARY OF THE INVENTION

One object of this invention is to provide improved mutant supersecreting yeast strains which permit high secretion levels of heterologous proteins and are non-leaky and non-reverting.

Another object of this invention is to provide simple proceedures for converting any haploid yeast strain into a non-leaky, non-reverting supersecreting strain.

Another object of this invention is to provide a method of obtaining supersecreting yeast strains by disrupting a gene in the strain to make the gene no longer capable of producing functional protein.

Another object of the present invention is to provide methods for cloning wild-type genes complementing supersecreting mutants.

Still another object of this invention is to provide the SSC1 gene which is in isolated form with the DNA sequence now provided.

Another object of this invention is to provide new methods for screening for supersecreting yeast mutants.

According to the invention supersecreting yeast cells or strains which have a gene which is disrupted making the gene incapable of producing a functional protein, are non-leaky and non-reverting and secrete high amounts of heterologous proteins. Preferably the gene can be SSC1. The gene can encode protein homologous to an ATPase. The gene can encode a protein which controls the mannose addition to glycoproteins.

A supersecreting SSC1 gene of *Saccharomyces cerevisiae* having the amino acid and nucleotide sequence of FIG. 5 has been isolated and clearly identified.

A method is provided for obtaining protein products from a yeast cell or strain capable of secreting a heterologous protein. The method comprises selecting a cell or strain to have an SSC1 gene modified to delete all codons distal to a Eco R1 site in SSC1. The strain is then cultured to secrete the protein.

In one of the processes of this invention, a supersecreting yeast strain which is non-reverting and non-leaky is obtained and the strain is grown to produce secreted protein products. The cells are derived from a line of cells where a gene has been changed by a) disrupting the gene with at least one other gene or b) deleting a portion of the gene, to make the line of cells non-reverting and non-leaky.

Wild-type alleles can be obtained by selecting a diploid strain homologous for a ssc mutation capable of sporulating at a first level and carrying at least one recessive drug resistant marker in a heterozygous state. The strains are subjected to sporulation conditions and resulting hapliod strains carrying the drug resistant marker and having resistance to a drug to which the marker provides resistance, are selected. In another method, cloning of the wild-type allele for an SSC gene is carried out by selecting an SSC strain carrying recombiant DNA and capable of secreting a heterologous protein at a first level. A library of plasmids carrying DNA fragments from a wild-type yeast genome is introduced to form a plurality of strains and resulting strains are selected which secrete the heterologous proteins at level below the first level. In another method, the selection is made by selecting resulting strains which add a second level of mannose greater than a first level of mannose secreted by the beginning strain.

BRIEF DESCRIPTION OF THE DRAWINGS

FIGS. 5A, 5B, 5C, 5D, 5E, 5G, and 5H show the DNA sequence and the translated protein sequence of SSC1 gene.

DESCRIPTION OF THE PREFERRED EMBODIMENTS

Figure 1:
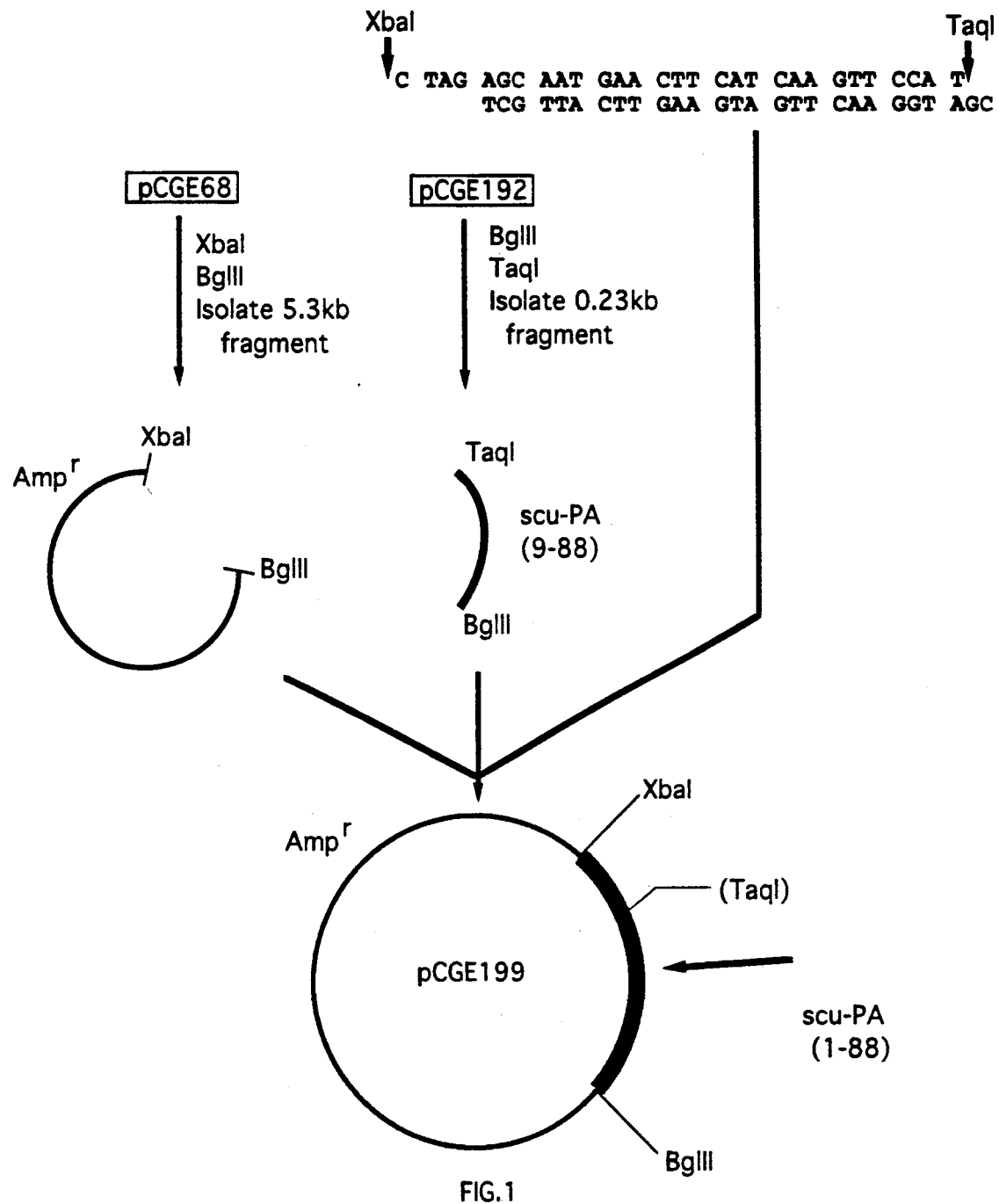
FIG. 1 is a schematic drawing illustrating the construction of plasmid pCGE199.

Now, methods have been discovered for isolating the DNA encoding the wild-type forms of these mutant genes which confer a supersecreting phenotype on yeast cells. These methods make it possible to determine if the version of the gene yielding a non-functional protein product is responsible for the useful supersecreting phenotype. We have determined that, lack of function creates a supersecreting strain. Methods are provided for replacing the appropriate gene in any haploid yeast strain with a version of the gene producing a non-functional product and thereby converting that yeast strain into a supersecreting yeast strain.

Not only is it possible, by following the methods of this invention, to convert any haploid yeast strain into a supersecreting strain, but these new supersecreting yeast strains also have advantages over those described by Duncan and Smith (1986, supra). For example, none of the new mutant alleles constructed by the methods of this invention will revert or be suppressed by frameshift, nonsense, or intragenic suppressors. Thus, they should permit larger scale fermentations and even continuous fermentations for long periods of time without the need for re-cloning of the fermentor seed stock.

The following methods are used to create and introduce into wild-type yeast strains versions of supersecreting genes which produce no functional protein product. Yeast integrative transformations occur virtually exclusively by homologous recombination, and it is possible to direct integrations to a particular genetic locus. For example, Orr-Weaver et al. (1983, Methods in Enzymology 101: 228-245) have shown that transformation of a yeast cell with a plasmid which has been linearized by a restriction endonuclease cut within a yeast gene on the plasmid will result in integration within that yeast gene in the yeast chromosomes most of the time. Extending this observation, Rothstein et al. (1983, Methods in Enzymology 101: 202-211) have shown that a linear fragment of yeast DNA will replace the homologous fragment in the yeast chromosomes. Thus, by means of these methods and with knowledge of the sequence of the gene of interest, it is possible to produce disruptions and deletions of that gene in the yeast cell by transformation.

For example, lys2 versions of any haploid yeast strain may be obtained by selection for growth on agar medium containing alpha-aminoadipate as the nitrogen source (Chatoo et al., 1979, Genetics 93: 51-65). The cloned LYS2 gene (Barnes & Thorner, 1986, Mol. Cell. Biol. 6: 2828-2838) may be placed in the coding region for a cloned SSC gene, thus disrupting the reading frame or replacing a portion of the codons. Transformation of the lys2 deficient host strain with a linear DNA fragment containing the SSC gene disrupted with the LYS2 gene and selection for Lys+ transformants will yield colonies in which the SSC gene has been replaced with the disrupted version.

New methods have also been discovered for conveniently identifying genes which may be mutated to produce supersecreting yeast strains. Surprisingly, it has been found that genes encoding proteins highly homologous to ATPases and those encoding proteins involved in the addition of mannose carbohydrate chains to other proteins may be mutated to produce supersecreting yeast strains. For example, the SSC1 protein, whose sequence is provided here, is highly homologous to many ATPases, and in addition, mutations in this gene surprisingly cause cells to secrete invertase bearing short mannose outer chains. Furthermore, cells carrying non-functional versions of the SSC1 gene are supersecreting mutants.

Cation-pumping ATPases are found in bacteria, fungi, and mammalian cells and are quite homologous with one another. These enzymes appear to participate in nutrient uptake and controlling concentrations of $H^+$, $Ca^{++}$, and $K^+$ in the cell. Genes for several yeast ATPases have been cloned (Serrano, R., Kielland-Brandt, M. C., and Fink, G. R., 1986, Nature 319: 689-693; Rudolph, H., Antebi, A., and Fink, G. R., 1988, 14th Int. Conf. on Yeast Genetics and Molecular Biology—Finland, S357, John Wiley & Sons, Ltd.), and the DNA and protein sequence of PMA1, the yeast plasma membrane ATPase, have been published (Serrano, R., et al., 1986, supra). Mutations eliminating PMA1 function are lethal to the yeast cell, and mutations of other related ATPases would be expected to have deleterious effects on the yeast cell because these proteins are likely to be involved in membrane transport and ion balance. Surpringly, we have found that mutations in the genes for some proteins which are highly homologous to ATPases, such as SSC1, result in a viable cell, and in particular, result in a cell which secretes many heterologous proteins much more efficiently.

Changes in the size of the mannose chain on glycoproteins are part of the phenotype of some supersecreting mutants, but it is clear that these mutations increase the secreted yield of many non-glycosylated proteins as well as glycoproteins. Thus the shorter mannose chains do not simply permit a smaller heterologus protein to escape more easily through the cell membrane or wall; rather, the effect must be on the physiology of the mutant cell itself.

Mutations in many different genes are known to affect the number of mannose residues added to glycoproteins in the yeast secretion pathway. Glycosylation occurs in two basic steps, and mutations have been described which affect each of the steps. First, a core unit of mannose residues, N-acetyl-glucosamine residues and glucose residues is built on a lipid intermediate and then transferred to the appropriate asparagine residues on glycoproteins in the endoplasmic reticulum of the cell. The alg mutations of Huffaker and Robbins (1982, J. Biol. Chem. 257: 3203–3210; 1983, Proc. Nat'l. Acad. Sci. USA 80: 7466–7470) affect many of the steps of that pathway. Second, the core unit is modified extensively after it is added to glycoproteins, and this occurs in the Golgi of the cell. A few mannose residues are removed, but then as many as several hundred are added in a long branched structure collectively known as the outer chains. The mnn mutants of Ballou and co-workers (C. E. Ballou, 1982, in "The Molecular Biology of the Yeast Saccharomyces: Metabolism and Gene Expression", Cold Spring Harbor Laboratory, N.Y., pp. 335–360) affect the steps of that pathway.

Surprisingly, we have found that mutations in the SSC1 gene affect not only secretion of some heterologous proteins but also the size of mannose chains on secretory proteins such as invertase. Conversely, we have also found that some strains carrying certain mnn and alg mutations not only secrete invertase with shorter mannose chains but also secrete some heterologous proteins more efficiently. Thus, a new characteristic of some cells which secrete heterologous proteins more efficiently has been discovered. Examination of strains which produce secretory proteins with shorter mannose chains will yield some strains with a supersecreter phenotype.

As a result of this invention, new methods for cloning the wild-type forms of recessive mutant genes conferring a supersecreting phenotype are available. For example, many ssc mutations, such as ssc1 and ssc2, when present in the homozygous form in a diploid cell, prevent that diploid cell from sporulating efficiently. A method is provided in this invention for cloning the wild-type form of the gene which complements this defective sporulation phenotype. This method is based on the principle that recessive drug resistance markers carried in the heterozygous state in a diploid which is homozygous for the ssc mutation will not appear in a haploid progeny spore from that diploid unless meiosis and sporulation have been completed successfully. By introducing DNA fragments from a wild-type yeast strain into that diploid via transformation, it is possible to select cells which have received a fragment which complements the sporulation defect and permits production of a haploid spore with one or more drug resistances.

Another new method for identifying DNA fragments carrying the wild-type forms of recessive mutant supersecreting genes involves direct screening for depression of secreted levels of a heterologous protein. For example, yeast cells carrying supersecreting mutations secrete human u-PA much more efficiently than wild-type cells. We have discovered a convenient method for measuring the approximate u-PA secretion level of individual yeast colonies derived from single cells. Supersecreting cells producing u-PA may be transformed with vectors carrying DNA fragments from a wild-type yeast strain, and transformants may be plated on the surface of membranes laid on a nutrient agar petri plate. After growth to colonies, the membrane may be moved to a different nutrient agar plate containing a salt at moderate ionic strength, and then moved to a bovine plasminogen-rich fibrin plate. The colonies will produce zones of clearing in the turbid fibrin network unless secretion of u-PA has been depressed by the presence of a wild-type gene complementing the ssc mutation.

In both of these cases, once a yeast colony containing a vector carrying a wild-type DNA fragment which complements the ssc mutation has been identified, it is possible to isolate the plasmid vector from that colony, to locate the wild-type SSC gene on that plasmid, to determine the sequence of that gene, and to build disrupting vectors which permit conversion of any haploid yeast strain to an ssc strain.

The following non-limiting examples are illustrative of the invention.

EXAMPLE 1

THE SSC1 GENE a. Building a suitable host strain for transformation and identification of a yeast DNA fragment carrying the SSC1 gene.

By taking advantage of the fact that diploid strains homozygous for the ssc1 mutation fail to sporulate efficiently, it was possible to slect the clones carrying yeast DNA fragments containing the SSC1 gene. The host strain used was CGY2014 with the following genotype: MATa/MATalpha ssc1/ssc1 +/can$^r$ lys2/+ leu2: :scu-PA+LEU/leu2: :scu-PA+LEU2 ura3/ura3/. The construction of strain CGY2014 is described below.

Strains CGY1465 (MATalpha leu2-3, 112 ura3 ssc1) and CGy1466 (MAT a leu2-3, 112 ura3 ssc1 strain, CGY1285 (STCC20750=MATalpha ura 3 ssc1-1), with a standard laboratory yeast strain CGY487 (MATa leu2-3, 112 ura3 can$^r$). CGY1285 was the product of ethylmethane sulfonate (EMS) mutagenesis of CGY998 (ATCC 20753; Matalpha ura3 his4/pCGS514), a standard labortory yeast strain which had been transformed with an autonomously replicating vector directing the expression of a yeast invertase-bovine prochymosin fusion gene. The resulting derivatives were screened for variants which secrete bovine prochymosin more efficiently (see EP 201208, and Smith, R. A., Duncan, M. J., and Moir, D. T., 1985, Science 229: 1219–1224). The canavanine resistance mutation (can') was provided by strain CGY487, but a suitable spontaneous can' mutation could also have been isolated by selecting for resistance to the poisonous arginine analog canavanine (see Fink, G. R., 1970, Methods in Enzymology 17A: 59–78).

A lys2 derivative of CGY1465 was obtained following EMS mutagenesis according to the method of Sherman, Fink & Hicks (1986, Methods in Yeast Genetics, Cold Spring Harbor Laboratory, N.Y., p. 9) by selecting for mutants which grow on agar minimal medium containing leucine, uracil, lysine and alpha-aminoadipate according to the protocol of Chatoo et al. (1979, Genetics 93: 51–65). This new derivative of CGY1465 was named CGY1998.

Both CGY1998 and CGY1466 were transformed with the integrating plasmid pCGS740 in order to introduce a transcriptional unit carrying the yeast phosphoglycerate kinase (PGK) promoter linked to the yeast invertase secretion signal coding region and the human single-chain urinary plasminogen activator (scu-PA) cDNA gene. Scu-PA is secreted very inefficiently from wild-type yeast cells, but much more efficiently from ssc1 yeast cells. Therefore, a depressed level of scu-PA secretion provided a second confirmatory screen for the presence in a ssc1 host of a DNA fragment encoding the complementing SSC1 gene.

Plasmid pCGS740 was derived from the common yeast integrating plasmid YIp5 (Struhl et al., 1979, Proc. Nat'l. Acad. Sci. USA 76: 1035–1039). It contains the PGK-promoted invertase secretion signal-scu-PA gene and a yeast LEU2 gene for selection of transformants. It was constructed as follows.

Two scu-PA cDNA clones were used for preparation of yeast plasmids: pCGE192 contains the sequence of Holmes et al. (1985, supra) from nucleoside 119 to 2304; pCGE195 contains the sequence of Holmes et al. (1985, Biotechnology 3: 923–929) from nucleoside 1 to 2304.

The natural scu-PA secretion signal codons were replaced with those of the yeast invertase secretion signal. This was accomplished as follows (see FIG. 1). Plasmid pCGE68 (Goff et al., 1984, Gene 27: 35–46) was used as a receiving vector for the desired scu PA encoding fragments. DNA of plasmid pCGE68 was cleaved with XbaI and BglII restriction endonucleases and an approximately 5.3 kb DNA fragment was purified by agarose gel electrophoresis.

An approximately 0.23 kb DNA fragment containing the codons for scu-PA amino acid residues 9 through 88 was isolated from plasmid pCGE192 following restriction with BglII and TaqI endonucleases and agarose gel electrophoresis. These two isolated DNA fragments were ligated together in the presence with the following synthetic oligodeoxynucleotide pair having ends cohesive with XbaI and TacI generated ends.

XbaI restriction endonuclease site directly prior to the first amino acid codon of mature scu-PA (FIG. 1).

Next, three DNA molecules were isolated and ligated together to yield a plasmid directing the synthesis and secretion of scu-PA by yeast (FIGS. 2A–B) First, DNA of plasmid pCGE199 was cut with restriction endonuclease XbaI, treated with single-strand specific nuclease S1 to remove the overhanging termini, and following removal of the S1, was further cut with endonuclease BglII. An approximately 0.26 kb fragment carrying the codons for the first 88 amino acid residues of mature scu-PA was isolated by agarose gel electrophoresis. The XbaI site was lost due to S1 nuclease trimming and is shown in parentheses in FIGS. 2A–B.

Figure 2A:
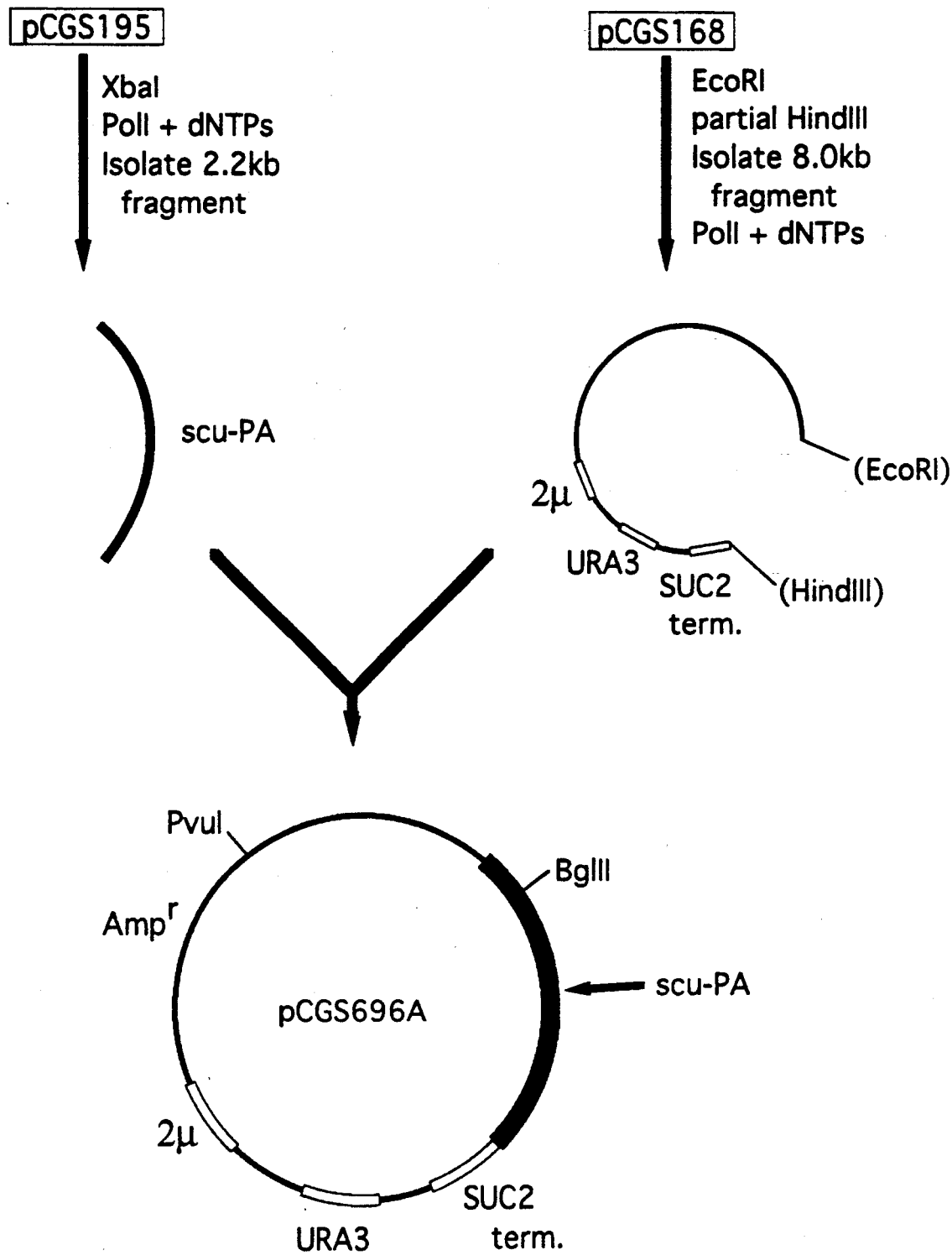
FIGS. 2A and 2B are schematic drawings illustrating the construction of plasmid pCGS715.
Figure 2B:
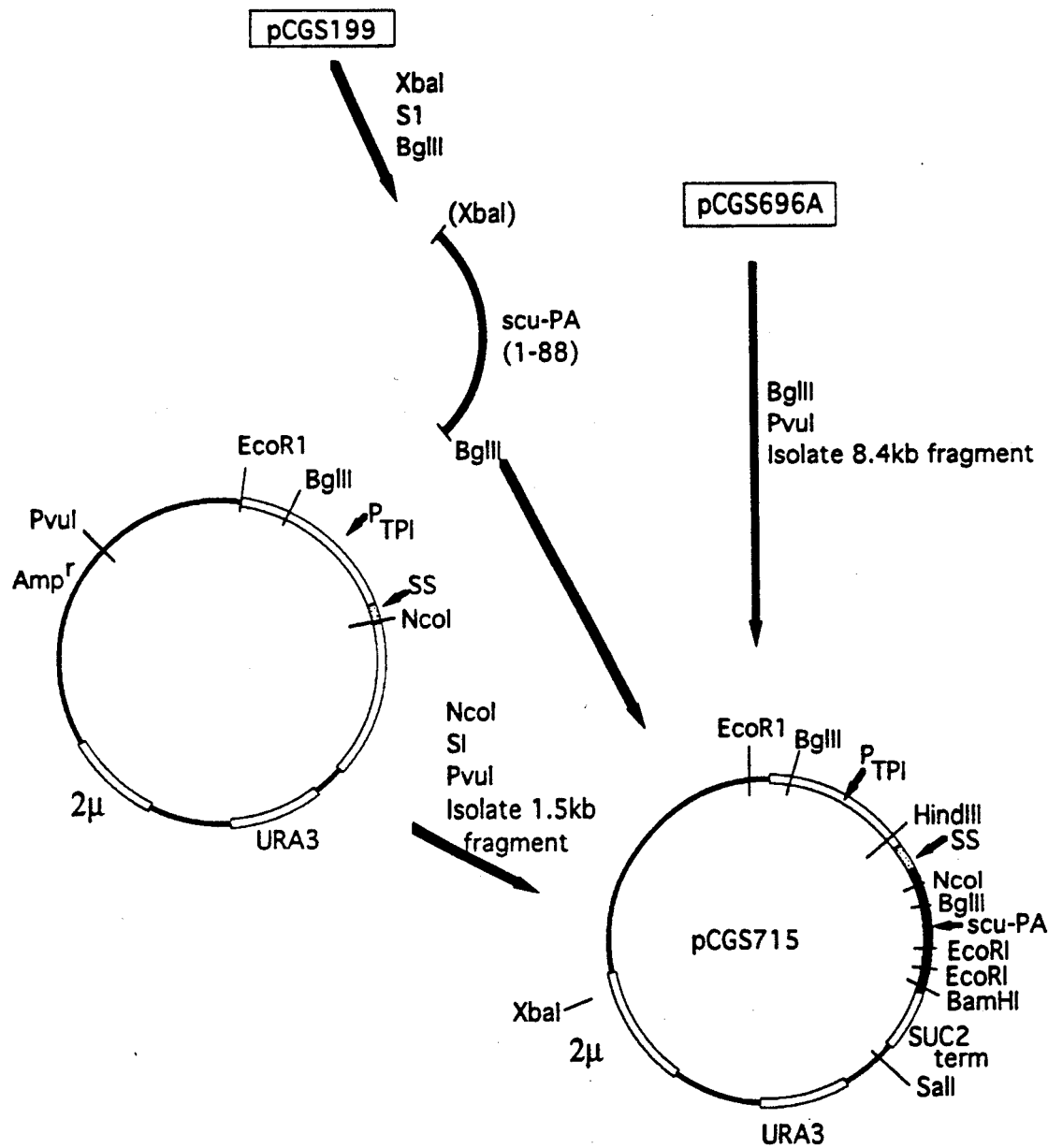

The remaining portion of the scu-PA was derived from plasmid pCGE195, another subclone of the scu-PA cDNA in pBR322, but first, the scu-PA cDNA was placed in a yeast-E. coli shuttle vector for more convenient access according to the following procedure (FIGS. 2A–B). DNA of the yeast-E. coli shuttle plasmid pCGS168 (Goff et al, 1984, Gene 27:35–46) was cut to completion with restriction endonuclease EcoRI and partially with nuclease HindIII, and the approximately 8 kb fragment containing the yeast-E. coli shuttle vector sequences together with the transcription terminator region from the yeast SUC2 gene was isolated by agarose gel electrophoresis. The EcoRI and HindIII cohesive ends were filled out with E. coli DNA polymerase I (Klenow fragment) in the presence of all four deoxynucleoside triphosphates. These two lost sites are denoted in parentheses in FIGS. 2A–B.

Next, DNA from plasmid pCGE195 was cut to completion with restriction endonuclease XbaI, the cohesive ends filled out with E. coli DNA polymerase I (Klenow fragment) in the presence of all four deoxynucleotide triphosphates, and the approximately 2.2 kb fragment containing the entire scu-PA cDNA was isolated by agarose gel electrophoresis. These two isolated fragments were ligated together and the ligation mixture was used to transform competent HB101 E. coli cells to ampicillin resistance. A colony carrying the desired plasmid pCGS696A was identified by restriction enzyme mapping of plasmids isolated from several transformant colonies.

The second DNA fragment needed for construction of the yeast expression and secretion vector was isolated from plasmid pCGS696A as follows (FIGS. 2A–B). DNA from plasmid pCGS696A was cut with restriction endonucleases BglII and PvuI, and an approximately 8.4 kb fragment carrying the yeast-E. coli shuttle vector sequences and most of the scu-PA cDNA was isolated by agarose gel electrophoresis.

Finally, plasmid pCGS685 provides the yeast triosephosphate isomerase promoter and the invertase secretion signal coding region with an NcoI access site at the

|   | 1 | 2 | 3 | 4 | 5 | 6 | 7 | 8 |   |   |
|---|---|---|---|---|---|---|---|---|---|---|
|   | ser | asn | glu | leu | his | gln | val | pro |   |   |
| 5' C | TAG | AGC | AAT | GAA | CTT | CAT | CAA | GTT | CCA | T 3' |
| 3' |   | TCG | TTA | CTT | GAA | GTA | GTT | CAA | GGT | AGC 5' |

The ligation mixture was used to transform competent HB101 E. coli cells to ampicillin resistance, and a colony carrying the desired plasmid pCGE199 was identified by restriction endonuclease mapping of plasmids derived from several transformant colonies. Plasmid pCGE199 carrys cDNA encoding the first 88 amino acid residues of mature scu-PA and having a unique end (FIGS. 2A–B). It is identical to plasmid pCGS681 (Moir and Dumais, 1987, Gene 56: 209–217) except that the NcoI site at the end of the invertase secretion signal coding region immediately follows the GCC codon for the final alanine residue of the secretion signal instead of falling between the two C residues of that codon. This was accomplished as for construction of pCGS681

(Moir and Dumais, 1987, supra) but after altering the sequence of the synthetic oligonucleotides appropriately. DNA of plasmid pCGS685 was cut with restriction endonuclease NcoI, treated with single-strand specific nuclease S1 to remove the overhanging termini, and following removal of the S1 nuclease, further restricted with endonuclease PvuI. An approximately 1.5 kb fragment carrying the yeast TPI promoter and invertase secretion signal was isolated by agarose gel electrophoresis.

The three isolated DNA fragments described in the preceding paragraphs were ligated together and the ligation mixture was used to transform competent HB101 E. coli cells to ampicillin resistance. A colony carrying the desired plasmid pCGS715 was identified by restriction enzyme mapping of plasmids isolated from several transformed colonies. Plasmid pCGS715 is an autonomously replicating yeast vector which directs the constitutive expression of the human scu-PA cDNA gene and whose presence can be maintained by demanding growth of a transformed ura3 strain in the absence of uracil.

The sequence of all DNA junctions resulting from ligation of S1 nuclease treated DNA fragments was checked at each step to insure that the S1 had trimmed the overlapping DNA strand correctly. If trimming was not correct, then plasmids from addional transformants were examined in order to find one in which trimming had occurred properly.

Next, the integrating yeast vector pCGS740 was constructed based on plasmid YIp5 (Struhl et al., 1979, Proc. Nat'l. Acad. Sci. USA 76: 1045-1039). In order to construct the vector, YIp5 was modified in the following manner. First, the URA3 gene was disrupted at its NcoI site with a functional LEU2 gene having NcoI sites at its ends, which was obtained in plasmid pJS34 from D. Fraenkel (Microbiology Department, Harvard Medical School, Boston, Mass.). YIp5 and pJS34 DNAs were cut with NcoI and treated with E. coli DNA polymerase I (klenow fragment) in the presence of all four deoxynucleotides in order to fill out the NcoI sites. The approximately 3.0 kb DNA fragment encoding the LEU2 gene was isolated from an agarose gel and blunt-end ligated to the cut YIp5 DNA. The resulting plasmid, YIp502, carrys a functional LEU2 gene and has no NcoI site. Next, the BamHI site in YIp502 was converted to a NcoI site by cutting with BamHI, filling out the overhanging ends with E. coli DNA polymerase I (klenow fragment) and all four deoxynucleotides, and ligating NcoI linkers (Collaborative Research, Inc. Bedford, Mass.). The resulting plasmid, YIp503, contains one new NcoI site in place of its former BamHI site.

DNA encoding the yeast PGK gene was obtained from D. Fraenkel (Microbiology Department, Harvard Medial School, Boston, Mass.) in plasmid pPGK1 (Kawasaki & Fraenkel, 1982, Biochem. Biophys. Res. Communic. 108: 1107-1112). An approximately 3.1 kb HindIII fragment containing the promoter and structural gene (see FIG. 1 of Hitzeman et al., 1982, Nucl. Acids Res. 10: 7791-7808) was subcloned into the HindIII site of pBR322 to yield plasmid pPGK102. DNA from plasmid pPGK102 was cut at the unique SacI site in the codon for PGK amino acid residue 154, and the DNA was trimmed with the exonuclease Bal31 (New England Biolabs, Beverley, Mass.). After treatment with Bal31, the plasmid was incubated with T4 DNA ligase in the presence of NcoI oligonucleotide linkers, and the DNA was used to transform competent E. coli HB101 to ampicillin resistance. Plasmid DNAs from several transformants were examined, and one trimmed back plasmid, designated pCGS521, had a NcoI linker fused directly to the A residue at −1 relative to the ATG translation start site of PGK.

The approximately 1.2 kb PGK promoter region was removed from pCGS521 by cutting with HindIII, treating with E. coli DNA polymerase I (klenow fragment) in the presence of all four deoxynucleotides, and following removal of the DNA polymerase I, cutting with NcoI, and agarose gel purification. This fragment was inserted into YIp503 in place of the approximately 0.35 kb DNA fragment between the HindIII and NcoI sites. The resulting plasmid, pPGK104, lacked a HindIII site due to the action of E. coli DNA polymerase (Klenow fragment) and all four deoxynucleotides on both of the HindIII ends of the DNA fragments used in the construction.

Three DNA fragments were ligated together to yield plasmid pCGS740. The approximately 0.28 kb fragment of pPGK104 between the NcoI and SalI sites was replaced by the approximately 2.2 kb HindIII to SalI fragment from pCGS715 (FIG. 2) and a pair of synthetic oligodeoxynucleotides bridging the NcoI to HindIII sites and providing the first 3 codons of the invertase signal. The 2.2 kb fragment from pCGS715 contains the last 16 codons of the invertase secretion signal fused to all of the scu-PA codons plus the invertase transcriptional terminator. The sequence of the synthetic oligo deoxynucleotides was as follows:

```
5' CATGATGCTTTTGCA      3'
3'      TACGAAAACGTTCGA 5'
```

Figure 3:
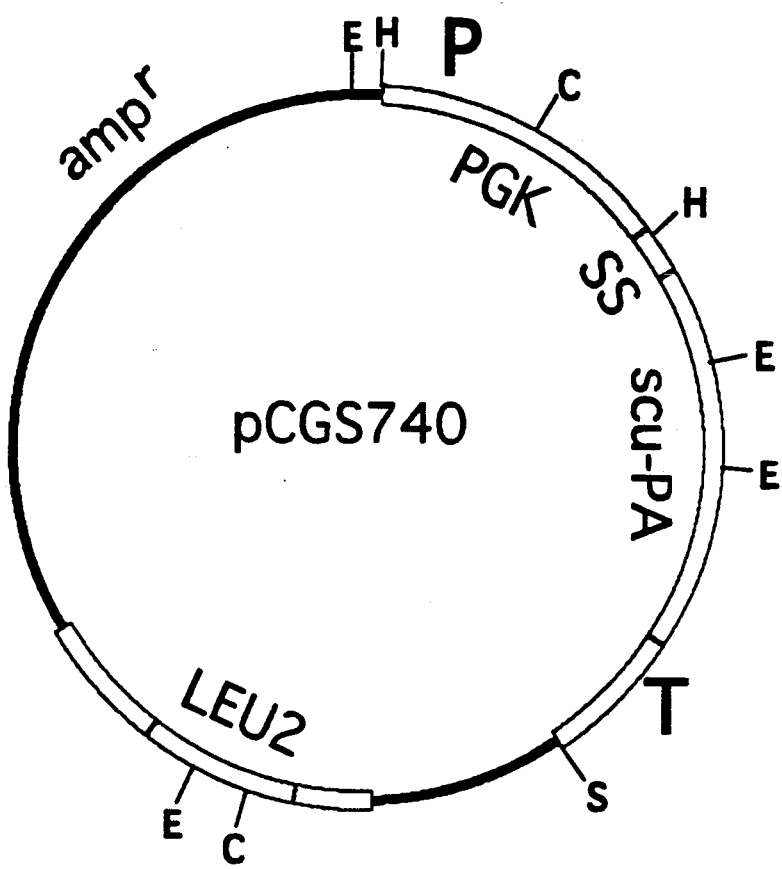
FIG. 3 is a schematic illustration of plasmid pCGS740.

The resulting plasmid pCGS740 shown in FIG. 3 provides a PGK promoted invertase signal sequence fusion to scu-PA whose presence can be selected by demanding LEU2 function. The sequence of the junctions between the PGK promoter, the invertase secretion signal coding region, and the scu-PA cDNA gene of plasmid pCGS740 are as follows.

```
                                            SUC2 secretion signal codons
PGK Promoter                                met leu leu gln ala phe leu phe leu leu
... ATCTACTTTTTACAACAAATATAAAACAACCATG  ATG CTT TTG CAA GCT TTC CTT TTC CTT TTG
                              former NcoI site
                                             HindIII site
```

```
                                        scu-PA codons
ala  gly  phe  ala  ala  lys  ile  ser  ala | ser  asn  glu  leu  his  gln  ...
GCT  GGT  TTT  GCA  GCC  AAA  ATA  TCT  GCC  AGC  AAT  GAA  CTT  CAT  CAA ... scu-PA codons
                                 as in Holmes, et al., 1985, supra
```

Transformation of CGY1998 and CGY1466 with pCGS740 was performed so that pCGS740 integrated into the yeast leu2 locus. This was accomplished by cutting pCGS740 DNA partially with the restriction endonuclease ClaI which cuts in the PGK and LEU2 genes (FIG. 3). Orr Weaver et al. (1983, Methods in Enzymology 101: 228–245) have shown that plasmids with a double-stranded break in a yeast gene frequently integrate into that gene in the yeast chromosomes after transformation of a suitable host strain. Accordingly, once-cut linear forms of pCGS740 were isolated from an agarose gel and used to transform CGY1998 and CGY1466 to leucine prototrophy. The location of the integrated pCGS740 plasmid in the yeast LEU2 gene was confirmed by Southern blot analysis of several transformants. The transformants CGY1991 and CGY1993, derived from strains CGY1998 and CGY 1466, respectively, were determined to have the required genotype and were crossed together to generate the diploid host strain CGY2014.

b. The homozygous ssc1 diploid CGY2014 is defective in sporulation

Sporulation of this ssc1 homozygous diploid was quite inefficient. For example, after incubation of the diploid on sporulation medium (see Sherman, Fink, & Hicks, 1986, Methods in Yeast Genetics, Cold Spring Harbor Laboratory, N.Y., p.167) for six days followed by mild treatment with glusulase and sonication to disrupt asci (Sherman, Fink & Hicks, 1986, supra. p.44), very few can$^r$ or alpha aminoadipate resistant spores were found. Both types of spores are expected at frequencies of 50% because can$^r$ and lys2 are unlinked genes which should segregate normally during meiosis and sporulation. Spores carrying both mutations, can$^r$ and alpha-aminoadipate resistance, are expected at 25%. In fact, can$^r$ spores were found at less than 2%, alpha-aminoadipate resistant spores were less than 17%, and spores carrying both resistances were found at less than 0.2%. By contrast, sporulation of a similar diploid which did not carry ssc1 mutations yielded the expected frequency of resistant spores. Thus, the diploid CGY2014 is sporulation deficient and is clearly a suitable host for tranformation with a library of yeast fragments and selection for those capable of causing normal sporulation.

c. Specific yeast DNA fragments will correct the sporulation deficiency of CGY2014.

Four libraries of plasmids carrying yeast DNA fragments were transformed into the host diploid CGY2014. These plasmid libraries were obtained from the Whitehead Institute for Biomedical Research at the Massachusetts Institute of Technology (Cambridge, Mass.) and are derived from pools A3, A4, C2, and C3 as described by Rose, Novick, Thomas, Botstein, and Fink (1987, Gene 60: 237–243). They each contain random fragments of yeast DNA inserted into the BamHI site of the autonomously replicating centromere-containing plasmid YCp50. Thus, on average, they are expected to be present in a yeast cell at about one copy per cell following introduction by transformation. This is important because many copies of any particular yeast gene could be toxic to yeast cells, and a clone harboring a plasmid carrying such a gene would not be obtained. Use of the centromere plasmid library insured that clones carrying the SSCI gene would not be lost due to toxicity at high copy number in a yeast transformant.

Plasmid DNA from each of the libraries was prepared by growing the E. coli cells harboring the plasmids, lysing the cells, and purifying the plasmid DNA on cesium chloride gradients containing ethidium bromide according to standard procedures (see for example, Maniatis, Fritsch, & Sambrook, 1982, Molecular Cloning, a Laboratory Manual, Cold Spring Harbor Laboratory, N.Y., p.86). The isolated DNA was used to transform CGY2014 to uracil prototrophy according to the procedure of Burgers and Percival (1987, Anal. Biochem. 163: 391–397).

Approximately 5,000 to 10,000 transformants from each of the four libraries were obtained. About 1,000 transformants from each library were picked and placed on sporulation medium (Sherman, Fink & Hicks, 1986, supra, p.167). After six days at 30° C., the colonies on sporulation medium were washed off with sterile water, asci were disrupted as described by Sherman, Fink & Hicks (1986, supra, p.44), and the spores were plated on SD medium containing canavanine (80 ug/ml), alpha-aminoadipate (0.2%), and lysine (0.003%). A few colonies grew on this selection medium, indicating that they had acquired resistance genes for both canavanine and alpha-aminoadipate, possibly because they had recombined the two genes through meiosis and sporulation. Specifically, four colonies from library A3, two from A4, and nine from C3 grew on the selection medium and were tested further.

d. These DNA fragments also depress the level of u-PA secreted.

The second test involved measuring the amount of scu-PA secreted by cells from these colonies. Those cells which carry the SSC1 gene should secrete less scu-PA than cells which do not carry an SSC1 gene to complement their ssc1 defect. The following assay for scu-PA secretion was performed. Strains were grown as patches overnight at 30° C. on SD+lysine agar medium (see Sherman, Fink & Hicks, 1986, supra), then inoculated into SD+lysine broth at about Klett 10 (green filter) and grown for 24 hr. Next, the strains were subcultured into SM-II+lysine at Klett 200 (green filter) and grown for an additional 24 hr. SM-II medium composition was as follows, with amounts given in grams per liter in parentheses (unless otherwise noted): glucose (80.0), KH$_2$(PO$_4$) (7.5), NaCl (3.0), (NH$_4$)$_2$HPO$_4$ (20.0), NH$_4$H$_2$PO$_4$ (20.0), myoinositol (0.3), yeast extract (Difco) (3.75), MgSO$_4$ (0.35), ZnSO$_4$ (0.03), CuSO$_4$ (0.0045), FeNH$_4$(SO$_4$)$_2$ (0.06), thiamine (0.052), pyridoxine (0.015), calcium pantothenate (0.0075), biotin (0.01), SAG 471 antifoam (Union Carbide) (0.25 ml/liter).

Finally, cells were pelleted by centrifugation, and 20 ul of broth was placed in the well of a bovine plasminogen-rich, fibrin agarose plate (Brakman, P., 1967, Fibrinolysis: a standardized fibrin plate method and a fibrinolytic assay of plasminogen. Scheltema & Holkema, Amsterdam). After incubation for 16 hr at 37° C., the diameter of the zone of clearing was compared to the diameters of zones produced by known standards, and the amount of scu-PA in the yeast broth was calculated by interpolation on a standard curve. Wild-type yeast strains secrete less than 3 international units (IU) of scu-PA per ml (note: this level is undetectable by the fibrin plate assay), while ssc1 strains typically secrete between 20 and 40 IU/ml under these conditions (this level produces zones of clearing reaching 13-17 mm diameter, including the 7 mm diameter well itself).

The results of this second test revealed that three colonies failed to secrete detectable levels of scu-PA. This result was consistent with the possibility that these colonies carry the SSC1 gene on the YCp50 plasmids which they received from the library. One of these colonies, CGY1982, was chosen for further analysis.

In order to demonstrate further that the plasmid carried by CGY1982 affects scu-PA secretion and thus may carry the SSC1 gene, strain CGY1982 was cured of its plasmid and also re-transformed with the plasmid. Presence of the plasmid is maintained by selection for uracil prototrophy since the host strain is ura3 and the plasmid carries the URA3 gene. The plasmid is lost during growth without selection for uracil prototrophy, and cells which have lost the plasmid can be selected by demanding growth on SD+lysine medium containing 5-fluoro-orotic acid according to the method of Boeke & Fink (1984, Molec. Gen. Genetics 197: 345). Derivatives of CGY1982 which had lost the plasmid and become Ura− were tested for secretion of scu-PA according to the protocol described above, and were found to secrete sufficient scu-PA to produce zones of clearing of about 13 mm. Thus, loss of the plasmid coincides with elevation of the scu-PA secretion level of the strain. One of these "cured" derivatives, CGY2003, was saved for further study.

The plasmid was isolated from strain CGY1982 as follows. Cells of strain CGY1982 were grown overnight in SD+lysine liquid medium, subcultured into 10 ml YPD liquid medium and grown to mid-log phase (about $2 \times 10^7$ cells per ml). Following the procedure of Sherman, Fink, and Hicks (1986, supra, p. 127), cells were harvested by centrifugation, lysed by treatment with the wall-digesting enzyme zymolyase, and the yeast DNA was partially purified. This preparation of yeast DNA was used to transform *E. coli* strain HB101 to ampicillin resistance. Plasmid DNA was prepared from several *E. coli* transformants as described previously (see Maniatis, Fritsch & Sambrook, 1982, supra). In practice, it has been observed that two or more different YCp50-based plasmids from the library can enter a single yeast cell during transformation and be maintained in that cell and its progeny for many generations. Accordingly, plasmid DNAs from several *E. coli* transformants were examined by restriction enzyme analysis to determine if all were identical or if several types of plasmids had been isolated. A single plasmid was obtained from CGY1892, and this plasmid was named pCGS861. If more than one type of plasmid had been found, then each would have been analyzed by the following methods in order to determine which one(s) carry the SSC1 gene.

When plasmid pCGS861 was used to transform the "cured" strain CGY2003 to uracil prototrophy, the transformants were found to secrete no detectable scu-PA when measured by the protocol described above. When plasmid YCp50, without a random yeast DNA fragment, was used to transform CGY2003, the resulting transformants secreted scu-PA at levels indistinguishable from those of CGY2003 itself. Thus, the presence of plasmid pCGS861, and in particular the presence of the yeast DNA insert in that plasmid, depresses scu-PA secretion. This result is consistent with fact that pCGS861 carries the SSC1 gene.

e. Characterization of plasmid pCGS861—generating a map of restriction endonuclease cleavage sites.

DNA of plasmid pCGS861 was digested with restriction endonucleases EcoRI, HindIII, and BamHI, both singly and in combination, and the approximate sizes of the cleavage products were deduced from their migration on agarose gels. From these results the map of restriction endonuclease cleavage sites shown in FIG. 4 was constructed. Plasmid pCGS861 is about 23.5 kb in size, consisting of an insert of about 15.5 kb of yeast DNA in the BamHI site of YCp50, which is itself about 8.0 kb in length. All of the insert and a portion of the YCp50 vector are shown in FIG. 4.

f. Localization of the SSC1 gene on plasmid pCGS861.

Figure 4:
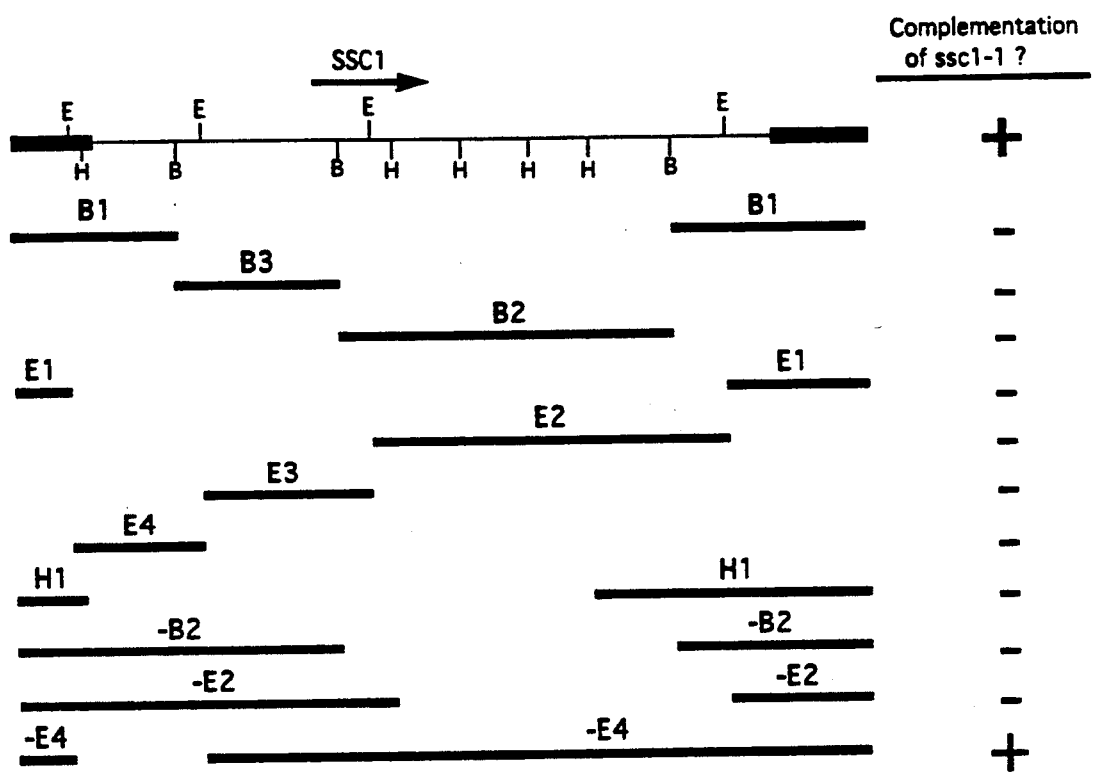
FIG. 4 depicts a restriction endonuclease cleavage map of the yeast DNA around the SSC1 locus inserted in plasmid pCGS681. This fugure also depicts smaller DNA fragments derived from pCGS681 and inserted into vector YCp50, and indicates whether they complement the ssc1-1 mutations for secretion of scu-PA by yeast cells.

Several new plasmids which contain portions of the yeast DNA insert in pCGS861 were built based upon the restriction endonuclease sites shown in FIG. 4. In particular, the three BamHI and four EcoRI sites were used to build plasmids B1, B2, B3, E1, E2, E3, E4, -B2, and -E2 shown in FIG. 4. In addition, one plasmid was built by cleavage with HindIII, and termed H1. All of these new plasmids consisted of the indicated fragments carried in YCp50. Each of these new plasmids was used to transform CGY2003 to uracil prototrophy, and the transformants were assayed for scu-PA secretion levels. None of the new plasmids complemented the ssc1-1 mutation in CGY2003 and depressed scu-PA secretion levels (see FIG. 4). Therefore, none of them carries the entire SSC1 gene.

Accordingly, a plasmid carrying a larger portion of the pCGS861 insert was constructed by partial EcoRI cleavage to yield plasmid -E4 (=E1+2+3). Strain CGY2003 transformed with this plasmid failed to secrete detectable levels of scu-PA. Therefore, this plasmid -E4, like pCGS861 itself, must carry the entire SSC1 gene. The only location for the SSC1 gene which is consistent with all of these results is one overlapping the BamHI and EcoRI sites as shown by the arrow on FIG. 4.

EXAMPLE 2

THE DNA SEQUENCE OF THE SSC1 GENE

The sequence of DNA bases in the region of plasmid pCGS681 encoding the SSC1 gene was determined by the dideoxy chain-terminating method of DNA sequencing (Chen, E. Y. and Seeburg, P. H., 1985, DNA 4: 165–170; Tabor, S. and Richardosn, C. C., 1987, Proc. Nat'l. Acad. Sci. USA 84: 4767–4771) by using synthetic oligodeoxynucleotide primers whose sequences were based first on known regions of YCp50 and then on regions of the SSC1 gene as they became known. The sequence together with its translated protein product are shown in FIGS. 5A–H.

EXAMPLE 3

HOMOLOGY BETWEEN THE SSC1 GENE PRODUCT AND ATPases

A search of published protein sequences revealed that the SSC1 gene product is highly homologous with but not identical to the following proteins (approximate percentage homology between the protein and the SSC1 gene product is given in parentheses): a sheep Na+/K+ATPase (30%) (Shull, G. E., Schwargz, A., and Lingrel, J. B., 1985, Nature 316: 691–695), Ca++-transporting ATPases from fast twitch (35%) and slow twitch (35%) rabbit muscle (Brandl, C. J., Green, N. M., Korczak, B., and MacLennan, D. H., 1986, Cell 44: 597–607; MacLennan, D. H., Brandl, C. J., Korczak, B., and Green, N. M., 1985, Nature 316: 696–700), and a K+-transporting ATPase from *E. coli* (30%) (Hesse, J. E., Wieczorek, L., Altendorf, K., Reicin, A. S., Dorus, E., and Epstein, W., 1984, Proc. Nat'l. Acad. Sci. USA 81: 4746–4750). In addition, the SSC1 gene product is highly homologous but not identical to another yeast protein, the PMA1 gene product which is a plasma membrane ATPase (Serrano, Keilland-Brandt, & Fink, 1986, supra). Therefore, the SSC1 gene encodes a protein which is quite homologous to ATPases from bacteria to mammals, and this protein is very likely to act as an ATPase in the yeast cell. As used in this application, "homologous" when applied to a comparison of a gene product and an ATPase is meant to indicate that at least 30% of the amino acid residues are identical and in identical relative position in the two proteins considered.

EXAMPLE 4

DISRUPTION OF THE SSC1 GENE RESULTS IN A SUPERSECRETING YEAST STRAIN

A yeast strain carrying a disruption of the SSC1 gene was constructed essentially as described for the actin gene by Shortle, et al. (1982, Science 217: 371–373). A 1.2 kb BamHI EcoRI restriction fragment known to lie within the SSC1 gene (FIG. 4) was inserted into the yeast plasmid vector YIp5 (Struhl, et al., 1979, supra), replacing the 378 bp BamHI-EcoRI fragment normally found there. This new vector, designated pCGS862, carries the yeast URA3 gene and can transform ura3 yeast strains to uracil prototrophy only by integration via homologous recombination into the yeast genome. Integration was directed to the SSC1 locus by linearizing pCGS682 with restriction endonuclease ClaI which cuts in the SSC1 coding DNA. Integration at the SSC1 locus disrupted the protein-coding portion of the SSC1 gene, generating a direct repeat of SSC1 gene sequences in which only the portion of the gene carried by the plasmid is duplicated. Consequently, each of the repeated copies of the SSC1 gene is incomplete, each terminating at one of the two restriction sites BamHI and EcoRI in the portion of the SSC1 gene on pCGS862.

Since disruption of an essential gene in this way would be a lethal event, both haploid and diploid strains were transformed to insure that viable transformants were obtained. Standard laboratory yeast strains which were wild-type for secretion were used for transformation. Their genotypes were as follows: MATalpha ura3 leu2 for the haploid and MATa/MATalpha ura3/ura3 leu2/leu2 for the diploid. Yeast transformations were performed by the method of Ito, et al. (1983, J.Bacteriol. 153: 163–168). The haploid and diploid yeast strains transformed also contained a scu-PA transcriptional unit on plasmid pCGS740 (EXAMPLE 1, supra) integrated at the LEU2 locus by the method described above (see EXAMPLE 1), so that scu-PA secretion could be monitored subsequently. Viable haploid transformants were obtained following transformation with pCGS862 selecting Ura+ colonies, indicating that SSC1 is not an essential gene.

To confirm the site of plasmid integration, gel-transfer hybridization experiments were carried out by the method of Southern (1975, J.Mol.Biol. 87: 503) as modified by Davis, et al. (1980, A Manual for Genetic Engineering/Advanced Bacterial Genetics, Cold Spring Harbor Press, N.Y.). Yeast DNA was prepared as described by Sherman, Fink & Hicks (1986, supra), p. 127), and separate aliquots were digested individually with EcoRl, HindIII, or PstI restriction endonucleases. The probe, the 1.2 kb BamHI EcoRI fragment of the SSC1 gene (FIG. 4), was labeled with $^{32}P$ by nick-translation (Davis et al., 1980, supra) in the presence of a labeled nucleotide. If pCGS862 integrates into and disrupts the SSC1 gene, fragments of the following expected sizes should hybridize with the probe, based on the known restriction sites in the SSC1 locus (see TABLE 1).

TABLE 1

| Enzyme used | Sizes of fragments expected to hybridize to the probe |
|---|---|
| EcoR1 | 4.7 kb for the intact locus |
|  | 4.7 & 6.3 kb for integration of pCGS862 at the SSC1 locus |
| HindIII | 1.9 kb for the intact locus |
|  | 8.2 kb for integration of pCGS862 at the SSC1 locus |
| PstI | >5.5 kb for the intact locus |
|  | >5.1 kb for integration of pCGS862 at the SSC1 locus |

DNA from several haploid transformants, including one designated CGY2197, yielded the fragments expected for a disrupted SSC1 gene. Therefore, this strain should no longer produce a functional SSC1 gene product. DNA from a few other transformants yielded bands expected for both the intact locus and the disrupted SSC1 locus. These transformants probably are aneuploid for the chromosome carrying the SSC1 gene, and therefore carry one disrupted SSC1 gene and one intact SSC1 gene. These transformants are not useful for practice of this invention because they do not secrete scu-PA more effeciently than wild type cells.

Transformant CGY2197 was analysed further to see if disruption of the SSC1 gene resulted in elevated levels of scu-PA secretion similar to those of strains bearing the ssc1-1 mutant allele (see EP 201208). External invertase was also examined to determine if SSC1 gene disruption affects mannose outer-chains in a fashion similar to that of the ssc1-1 mutant allele.

The amounts of scu-PA secreted from CGY2197 and its untransformed parent were determined as described in EXAMPLE 1 above. Culture broths were placed in wells in fibrin plates, incubated at 37° C. for 16 hours, and the diameters of zones of clearing were measured. CGY2197 was found to secrete scu-PA at levels similar to those of strains bearing the ssc1-1 allele. Culture broth from the growth of CGY2197 cells produced fibrin lysis zones of from 13 to 15 mm in diameter. Culture broths from the parent strain bearing the same scu-PA transcription unit but a functional SSC1 gene, produced no detectable fibrin lysis zone (i.e., less than 7 mm in diameter). Thus, disruption of the SSC1 gene to yield a non-functional gene results in elevated secretion of scu-PA.

EXAMPLE 5

YEAST STRAINS CARRYING THE sscl-1 ALLELE OR DISRUPTIONS OF THE SSC1 GENE SECRETE INVERTASE BEARING SHORT MANNOSE CHAINS Yeast strains bearing the sscl-1 or the disrupted sscl mutant alleles produce invertase bearing short mannose outer chains, similar to those found in mnn9 mutant strains (Ballou, et al., 1980, J.Biol.Chem. 255: 5986-5991; Tsai, et al., 1984, J.Biol.Chem. 259: 3805-3811), but complementation analysis indicates that the sscl and mnn9 mutations define different genes. The approximate size of mannose outer chains on external invertase produced by several yeast strains was determined by analysis on native polyacrylamide gels as described by Kaiser, et al. (1987, Science 235: 312-317) except that:

(i) Invertase activity was first quantitated by the method of Goldstein and Lampen (1975, Methods in Enzymology 42C: 505) as modified by Carlson, et al. (1984, Genetics 107: 19) and Celenza and Carlson (1984, Mol. Cell. Biol. 4: 49). Sufficient cells were lysed and 1000-1100 U of invertase were loaded per gel lane.

(ii) Cells were lysed in 100 ul of lysis buffer.

(iii) Crude extracts were heated to 50° C. for 30 minutes prior to loading on 4% native polyacrylamide gels, in order to convert the invertase to a single oligomeric form (Esmon, et al., 1987, J. Biol. Chem. 262: 4387-4394).

Figure 6:
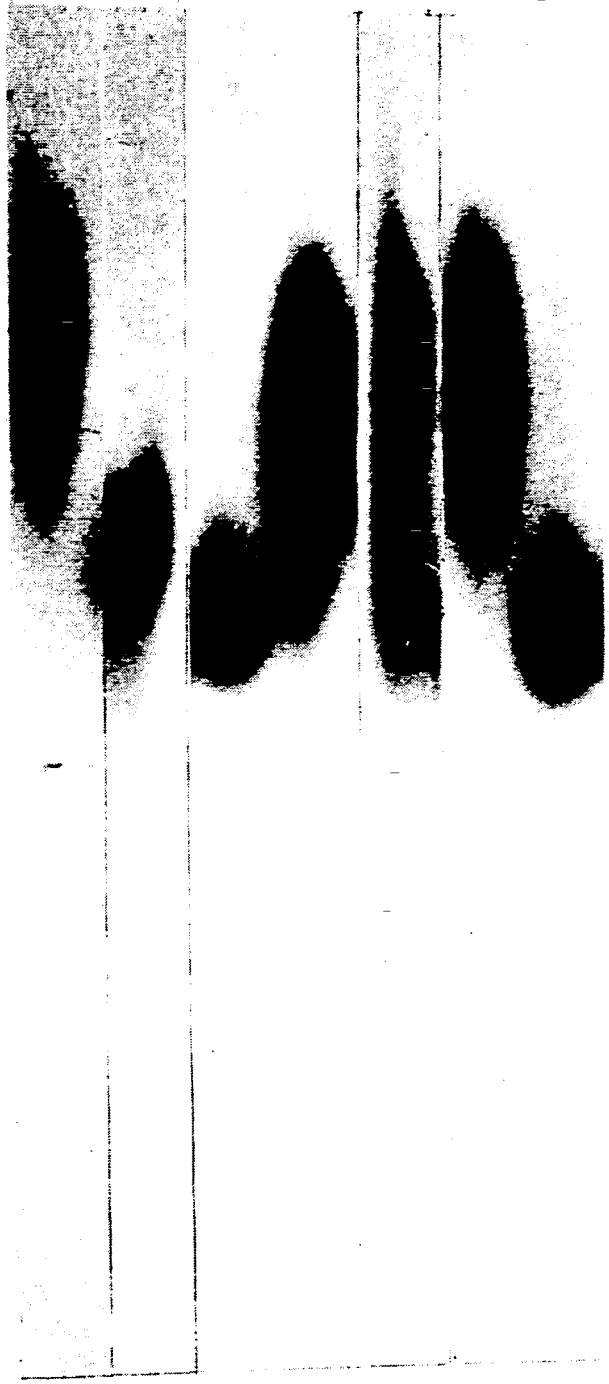
FIG. 6 shows a non-denaturing polyacrylamide gel separation of invertase from yeast strains carrying mutations in various genes involved in mannose addition to glycoproteins.

Strains with the following secretion and glycosylation genotypes were used in this analysis (see FIG. 6). CGY489 and CGY1974 (lanes a and f, respectively) are wild-type for glycosylation and secretion; CGY1028 (lane c) carries the sscl-1 mutation; CGY2197 (lane g) is wild-type strain CGY1974 which has been transformed with pCGS682 to disrupt the SSC1 gene; CGY2202 (lane d) is CGY1028 transformed with pCGS861 carrying the functional SSC1 gene; CGY1570 (lane b) carries the mnn9 mutation; CGY2216 (lane e) is a diploid derived from cross of a mnn9 SSC1 strain by a MNN9 sscl-1 strain.

The results shown in FIG. 6 reveal that CGY2216 (lane e) adds wild-type mannose outer chains to invertase, proving that strains carrying sscl-1 and mnn9 complement each other for mannose addition to invertase, and therefore that sscl and mnn9 define different genes. Strains carrying the sscl-1 allele and those which carry disrupted SSC1 genes add smaller mannose chains to invertase than strains carrying mnn7, mnn8, or mnn10 (Ballou, 1982, supra); thus, the SSC1 gene must be distinct from these other known mannose chain truncating mutations as well. CGY2197 (lane g) adds shorter mannose outer chains to invertase, similar to those of CGY1028 (lane c) which bears the sscl-1 allele. Thus, SSC1 gene disruption yields a strain with the same glycosylation phenotype as strains carrying the sscl-1 mutation—namely, smaller mannose outer chains on secreted invertase.

The tendency to add short mannose outer chains to invertase conferred by the sscl-1 mutation is also complemented by the SSC1 gene on plasmid pCGS861 because CGY2202 produces invertase with the wild-type pattern of long mannose outer chains while CGY1028 produces invertase with shorter mannose chains (lanes d and c, respectively). Thus the presence of pCGS861 restores mannose outer chain glycosylation of invertase in yeast strains bearing the sscl-1 mutant allele.

EXAMPLE 6

OTHER GLYCOSYLATION MUTATIONS AFFECT SECRETION OF FOREIGN PROTEINS

Many yeast strains carrying mutations which affect the size of mannose chains added during glycosylation secrete heterologous proteins and glycoproteins more efficiently. For example, the strains shown in TABLE 2 below were transformed to uracil prototrophy with plasmid pCGS715 which directs the production and secretion of human u-PA, and levels of secreted u-PA were examined by means of the bovine plasminogen-rich fibrin plate assay (EXAMPLE 1, supra). Strains were inoculated into SM-II (see EXAMPLE 1, supra) at Klett 100 (green filter) and grown for 48 hr at 30° C. Twenty microliters of cell-free broth was placed in the well of a fibrin plate and zone diameters were measured after 16 hr at 37° C.

TABLE 2

| Strain | Genotype | Approximate Number of Mannose Residues Added to Each ASN | Fibrinolytic Zone (mm) | u-PA (IU/ml) |
|---|---|---|---|---|
| CGY339 | wild-type | >100 | 7.0 | <2.0 |
| CGY1585 | sscl-1 | ~12 | 15.5 | 30 |
| CGY2070 | mnn1 mnn9 | ~8 | 14.0 | 21 |
| CGY1881 | sig3 mnn9 | ~7 | 14.5 | 23 |

While the level of u-PA secretion does not directly correlate with the predicted size of the mannose chains added to proteins by these mutants, nevertheless, strains which add fewer mannose residues do in fact secrete significantly more u-PA than wild-type strains.

EXAMPLE 7

A METHOD FOR DISRUPTING THE SSC1 GENE IN ANY HAPLOID YEAST STRAIN

By incorporating the LYS2 gene into the coding region of the SSC1 gene, it is possible to convert any haploid yeast strain to an sscl strain. This is because of a unique feature of yeast LYS2 biology. Chatoo et al. (1979, supra) and Sherman, Fink & Hicks (1986, supra) have shown that it is possible to select for lys2 mutations in any haploid yeast strain by simply plating it on minimal medium supplemented with lysine and alpha-aminoadipic acid as the nitrogen source. Colonies which grow are checked to see that they fail to complement a known lys2 strain. The lys2 deficient strain can then be transformed with an SSC1 disrupting plasmid containing the LYS2 gene by selecting for Lys+ colonies. By building the SSC1 disrupting vector in the following manner, it will disrupt the SSC1 gene by integrative transformation according to the method of Orr-Weaver et al. (1983, supra)

Three DNA fragments are ligated together to yield plasmid pDISsscl. Plasmid pCGS862 (supra, about 6.5 kb) carrying a portion of the SSC1 gene is linearized by restriction with endonuclease EcoRI. Next, the LYS2 gene is excized from plasmid YIp600 (Barnes and Thorner, 1986, supra) by restriction with EcoRI and HindIII, followed by isolation of the approximately 5 kb fragment from an agarose gel. Finally, plasmid YCp50(E2) (EXAMPLE 1f; FIG. 4) is cut to completion with restriction endonuclease EcoRI and cut partially with HindIII, and an approximately 6.4 kb fragment carrying all of the insert in YCp50(E2) except the smallest EcoRI to HindIII fragment (left most in FIG. 4) is isolated from an agarose gel. These three fragments are ligated together, and the ligation mixture is used to transform *E. coli* HB101 to ampicillin resistance. Plasmid DNAs from several transformants are examined by restriction endonuclease mapping, and one plasmid pDISssc1 is found which contains the LYS2 gene ligated between the two portions of the SSC1 gene.

A lys2 version of wild type yeast strain CGY150 (MATalpha ura3-52 leu2-3) is obtained by selection on medium containing alpha-aminoadipic acid (Sherman, Fink, & Hicks, 1986, supra). This lys2 version of CGY150 called CGY150L is transformed to Leu+ with plasmid pCGS740 (EXAMPLE 1, supra). Next, the resulting strain CGY150L/pCGS740 carrying an integrated scu-PA transcriptional unit is transformed with a linear fragment of pDISssc1. Plasmid DNA of pDISssc1 is cut with restriction endonuclease ClaI and used to transform CGY150/pCGS740, selecting Lys+ colonies. A Southern blot confirms that the chromosomal SSC1 gene of one of the new transformants CGY150L/pCGS740/pDISssc1 now contains the LYS2 gene inserted into it. Both CGY150L/pCGS740 and CGY150L/pCGS740/pDISssc1 are grown in SM-II broth (see EXAMPLE 1), and 20 ul of conditioned broth are placed in wells in a bovine plasminogen rich fibrin agar plate. Broth from CGY150L/pCGS740/pDISssc1 produces a much larger fibrin lysis zone than broth from CGY150L/pCGS740. Thus, disruption of the SSC1 gene in a wild-type yeast strain produces a supersecreting strain which secretes human scu-PA more efficiently than a wild-type strain.

EXAMPLE 8

STRAINS CARRYING A DISRUPTED SSC1 GENE SECRETE BOVINE PROCHYMOSIN MORE EFFICIENTLY

A lys2 version of wild-type yeast strain CGY150 (MATalpha ura3-52 leu2-3) is obtained as described in EXAMPLE 7 above and named CGY150L. It is next transformed with a linear fragment of plasmid pDISssc1 disrupting the SSC1 gene. Plasmid DNA of pDISssc1 is cut with restriction endonuclease ClaI and used to transform CGY150 selecting Lys colonies. A Southern blot confirms that the chromosomal SSC1 gene of one of the new transformants CGY150L/pDISssc1 now contains the LYS2 gene inserted into it. This SSC1 disrupted strain is transformed to Ura+ with plasmid pCGS514 (Duncan and Smith, 1986, European Patent Application EP 201208; note that plasmid pCGS514 is found in yeast strain CGY998 deposited in the American Type Culture Collection as accession number ATCC 20753) which provides a bovine prochymosin gene fused to the yeast invertase secretion signal and under the direction of the yeast triosephosphate isomerase promoter.

Levels of prochymosin secreted by CGY150L and CGY150L/pDISssc1 both transformed with plasmid pCGS514 are compared by following the growth and assay procedure of Smith, Duncan and Moir (1985, supra). Strain CGY150L/pDISssc1 secretes significantly more prochymosin than strain CGY150L when they are both transformed with plasmid pCGS514. Thus, disruption of the SSC1 gene in a wild-type yeast strain produces a supersecreting strain which secretes bovine prochymosin more efficiently than a wild-type strain.

EXAMPLE 9

CLONING THE SSC2 GENE BY SCREENING FOR DEPRESSION OF u-PA SECRETION

A lys2 version of strain CGY1291 (MATalpha his4 ura3-52 ssc2-1 = ATCC 20752) is isolated by selection for colonies which grow on minimal medium supplemented with histidine, uracil, lysine, and containing alpha-aminoadipic acid as the nitrogen source according to the method of Sherman, Fink, and Hicks (1986, supra, pp.49–52). Failure to complement an authentic lys2 strain obtained from the Yeast Genetic Stock Center at U.C. Berkeley demonstrates that the colony chosen, DMY129, contains a lys2 mutation.

A yeast integrating plasmid carrying the LYS2 gene and a human scu-PA transcriptional unit is constructed as follows. An approximately 4.7 kb DNA fragment containing the PGK promoter, the yeast invertase secretion signal, the human scu-PA cDNA gene, and the yeast invertase terminator are derived from plasmid pCGS740 (EXAMPLE 1, supra) by partial restriction with HindIII followed by complete restriction with SalI and electrophoretic separation on an agarose gel. An approximately 8.6 kb DNA fragment containing a functional LYS2 gene and pBR322 sequences is derived from plasmid YIp600 (Barnes and Thorner, 1986, supra) by complete restriction with endonucleases HindIII and SalI. The two fragments are ligated together and the ligation mixture is used to transform *E. coli* HB101 to ampicillin resistance. Plasmid DNAs are examined from a few transformants and one, designated YIp611, is determined to carry the entire scu-PA transcriptional unit replacing the approximately 0.8 kb HindIII to SalI DNA fragment of YIp600.

Strain DMY129 is transformed to Lys+ with DNA of plasmid YIp611 which is first linearized in the LYS2 gene by restriction with XhoI. A typical Lys+ transformant, DMY130, is shown to secrete detectable scu-PA by measuring the zone of fibrin lysis created by broth from a transformant culture in the bovine plasminogen-rich fibrin plate (EXAMPLE 1, supra).

Strain DMY130 is transformed to Ura+ by the method of Ito et al. (1983, J. Bacteriol. 153: 163–168) using plasmid DNA from pools A3, A4, C2, and C3 of the YCp50 based yeast fragment library of Rose et al. (1987, supra). After they have grown into colonies, transformants are washed off of the plates with sterile water and replated on the surface of sterile nylon filters laid on SD medium supplemented with histidine (Sherman, Fink and Hicks, 1986, supra, p. 164). After three days at 30° C., the nylon filters are peeled off of the plates and laid, colony-side up, on the surface of agar plates containing SM-II medium. SM-II medium composition is as follows, with amounts given in grams per liter in parentheses (unless otherwise noted): glucose (80.0), $KH_2PO_4$ (7.5), NaCl (3.0), $(NH_4)_2HOP_4$ (20.0), $NH_4H_2PO_4$ (20.0), myoinositol (0.3), yeast extract (Difco) (3.75), $MgSO_4$ (0.35), $ZnSO_4$ (0.03), $CuSO_4$ (0.0045), $FeNH_4(SO_4)_2$ (0.06), thiamine (0.052), pyridoxine (0.015), calcium pantothenate (0.0075), and biotin (0.01). After two-four days at 30° C., the nylon filters are peeled off and laid, colony-side up, on the surface of a bovine plasminogen-rich fibrin plate (EXAMPLE 1, supra). Within four to sixteen hours at 37° C. zones of fibrin lysis will form under the colonies which are of genotype ssc2. Some colonies will not form zones of lysis or will form them much more slowly than the majority of colonies. A few of these slower zone forming colonies contain the SSC2 gene on a YCp50-based plasmid.

Curing of the YCp50-based plasmid from a few of these slow zone-forming transformants by, for example, growth on medium containing 5-fluoro-orotic acid according to the method of Boeke et al. (1984, Mol. Gen. Genet. 197: 345-346) results in colonies which now secrete scu-PA as efficiently as the untransformed DMY130 strain. These colonies contained a YCp50-based plasmid carrying the SSC2 gene.

The plasmid is isolated from the yeast strain and cloned in E. coli exactly as described for pCGS861 (EXAMPLE 1, supra). The SSC2 gene is localized on the plasmid by subcloning smaller and smaller fragments and testing them for the presence of a functional SSC2 gene by asking if they complement strain DMY130 for efficient secretion of scu-PA. The DNA sequence of the SSC2 gene is determined by using the same methods used for determining the sequence of the SSC1 gene. The LYS2 gene is inserted into the reading frame of the SSC2 gene to create a plasmid which can be used to disrupt SSC2 in any haploid yeast strain as described for pDISssc1 (EXAMPLE 7, supra). Strains which are disrupted at the SSC2 locus secrete many heterologous proteins more efficiently than wild-type strains. Furthermore, supersecretion by the SSC2-disrupted strains does not revert and is not suppressed by frame-shift, nonsense, or intragenic suppressors.

The above examples show specific emobodiments of selecting supersecreting strains for obtaining increased production of foreign proteins in yeast. The method is applicable to all yeast cells. In each case, after carrying out the procedures of this invention, screening is carried out to determine yeast cells which have been changed so as to provide at least a two-fold increase in secretion of foreign proteins.

The specific methods of cloning and growing cells to obtain increased secretion of proteins can vary greatly as known in the art. For example yeast can be grown under a variety of culturing or fermentation conditions well known to those skilled in the art.

In all cases it is useful to obtain at least a two fold increase in secretion of proteins by the yeast treated according to the methods of the invention.

We claim:

1. A supersecreting *saccharomyces cerevisiae* yeast cell exhibiting at least two-fold increased translocation of a heterologous protein through its secretory pathway and having an SSC1 gene which is disrupted or deleted making said gene incapable of producing a functional protein and rendering the supersecretion properties of said cell non-leaky and non-reverting.

2. A method of obtaining protein products from an SSC1 yeast cell strain capable of secreting a heterologous protein, said method comprising selecting said cell strain to have the SSC1 gene of FIGS. 5A–H modified by deletion of all codons distal to the EcoRI site which begins at nucleotide 1613 and culturing said strain to secrete said protein products.

3. A process of using a supersecreting yeast strain to obtain heterologous protein products, said process comprising culturing under conditions suitable for expression of said heterologous protein products a *Saccharomyces cerevisiae* yeast cell in which the SCC1 gene has been either a) disrupted with at least one other gene or b) partially deleted such that the resulting cell exhibits at least 2-fold translocation of said heterologous gene products through its secretory pathway and the supersecretion properties are non-reverting and non-leaky.

* * * * *